United States Patent

Wroblowsky et al.

Patent Number: 5,174,808
Date of Patent: Dec. 29, 1992

[54] HERBICIDAL PYRAZOLIN-5-ONE DERIVATIVES, COMPOSITIONS AND USE

[75] Inventors: Heinz-Jürgen Wroblowsky, Langenfeld; Peter Babczinski, Wuppertal; Klaus Lürssen, Bergisch Gladbach; Hans-Joachim Santel, Leverkusen; Robert R. Schmidt, Bergisch Gladbach, all of Fed. Rep. of Germany

[73] Assignee: Bayer Aktiengesellschaft, Leverkusen, Fed. Rep. of Germany

[21] Appl. No.: 610,597

[22] Filed: Nov. 8, 1990

[30] Foreign Application Priority Data

Dec. 14, 1989 [DE] Fed. Rep. of Germany ....... 3941240

[51] Int. Cl.$^5$ ................... A01N 43/56; C07D 231/22
[52] U.S. Cl. ................................ 71/92; 71/90; 546/256; 546/279; 548/370.1; 548/365.7; 548/364.1; 548/364.4; 548/364.7
[58] Field of Search ............... 546/256, 279; 548/364, 548/367; 71/90, 92

[56] References Cited

U.S. PATENT DOCUMENTS 4,909,827 3/1990 Gehring et al. ................. 548/365

FOREIGN PATENT DOCUMENTS 0274642 7/1988 European Pat. Off. .

OTHER PUBLICATIONS

Chemical Abstracts, vol. 61 Dec. 1964, No. 14659h.
Hennig et al, Chemical Abstracts, vol. 110 (1989) No. 87383p.

Primary Examiner—Robert W. Ramsuer
Attorney, Agent, or Firm—Sprung Horn Kramer & Woods

[57] ABSTRACT

Herbicidal pyrazolin-5-one derivatives of the formula

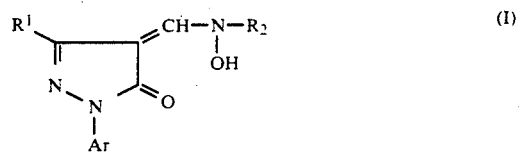

in which
$R^1$ represents alkyl, cycloalkyl, halogenoalkyl, alkenyl, alkynyl, alkenyl or alkynyl substituted by optionally substituted phenyl, halogenoalkenyl, alkoxy, alkoxyalkyl, alkylthioalkyl, alkylsulphonylalkyl, alkylsulphinylalkyl, alkoxycarbonylalkyl, in each case optionally substituted aryl, aralkyl, aryloxyalkyl or arylthioalkyl, an optionally substituted heterocycle, heterocyclylalkyl or the —NH—CO—$R^3$ or —CO—O—$R^4$ groups, in which $R^3$ and $R^4$ in each case independently of one another represent alkyl or aryl,
$R^2$ represents hydrogen, alkyl, cycloalkyl, halogenoalkyl, alkenyl, alkinyl, halogenoalkenyl, alkoxyalkyl, alkylthioalkyl, alkylsulphonylalkyl, alkylsuslphinylalkyl or alkoxycarbonylalkyl and
Ar represents optionally substituted aryl or a heterocycle which is optionally substituted and optionally fused, excluding the compounds 1-(3-chlorophenyl)-3-methylthiomethyl-4-(N-hydroxyaminomethylidene)-pyrazoline-5-one, 1-(4-chlorophenyl)-3-methylthiomethyl-4-(N-hydroxyaminomethylidene)-pyrazolin-5-one, 1-(4-trifluoronethylphenyl-3-methylthiomethyl-4-(N-hydroxyaminomethylidene))-pyrazolin-5-one and 1-(4-n-nitrophenyl)-3-methylthiomethyl-4-(N-hydroxyaminomethylidene)-pyrazolin-5-one.

7 Claims, No Drawings

HERBICIDAL PYRAZOLIN-5-ONE DERIVATIVES, COMPOSITIONS AND USE

The invention relates to new pyrazolin-5-one derivatives, to a process for their preparation and to their use as herbicides.

It has already been disclosed that certain pyrazolin-5-one derivatives have herbicidal properties (compare DE-OS (German Published Specification) 2,513,750).

In addition, the herbicidal and fungicidal activity of certain pyrazolin-5-one derivatives has been disclosed (compare EP-A 274,642).

However, the herbicidal activity of these previously known compounds against problem weeds, like their tolerability to important cultivated plants, is not completely satisfactory in all areas of application.

New pyrazolin-5-one derivatives of the general formula (I)

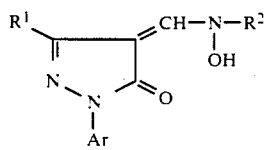

in which
$R^1$ represents alkyl, cycloalkyl, halogenoalkyl, in each case optionally substituted alkenyl or alkynyl, optionally substituted phenyl being selected as the substituted, halogenoalkenyl, alkoxy, alkoxyalkyl, alkylthioalkyl, alkylsulphonylalkyl, alkylsulphinylalkyl, alkoxycarbonylalkyl, in each case optionally substituted aryl, aralkyl, aryloxyalkyl or arylthioalkyl, an optionally substituted heterocycle, heterocyclylalkyl or the —NH—CO—$R^3$ or —CO—O—$R^4$ groups, in which $R^3$ and $R^4$ in each case independently of one another represent alkyl or aryl, $R^2$ represents hydrogen, alkyl, cycloalkyl, halogenoalkyl, alkenyl, alkynyl, halogenoalkenyl, alkoxyalkyl, alkylthioalkyl, alkylsulphonylalkyl, alkylsulphinylalkyl or alkoxycarbonylalkyl and Ar represents optionally substituted aryl or a heterocycle which is optionally substituted and/or optionally fused,
excluding the compounds 1-(3-chlorophenyl)-3-methylthiomethyl-4-(N-hydroxyaminomethylidene)-pyrazolin-5-one, 1- (4-chlorophenyl)-3-methylthiomethyl-4-(N-hydroxyaminomethylidene)-pyrazolin-5-one, 1-(4-trifluoromethylphenyl)-3-methylthiomethyl-4-(N-hydroxyaminomethylidene)-pyrazolin-5-one and 1-(4-nitrophenyl)-3-methylthiomethyl-4-(N-hydroxyaminomethylidene)-pyrazolin-5-one, have been found.

The compounds of the formula (I) can exist as geometrical isomers (E/Z isomers) or isomer mixtures of differing composition. The invention relates both to the pure isomers and to the isomer mixtures.

In addition, in the case in which $R^2$ represents hydrogen, the compounds of the formula (I) according to the invention can be present in tautomeric equilibrium:

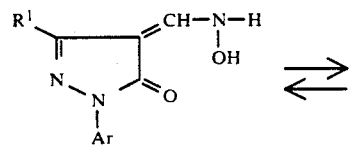 ⇌ 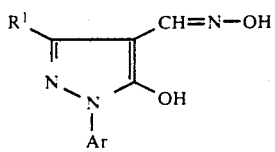

In what follows, for the sake of simplicity compounds of the formula (I) are always referred to although both the pure compounds and their mixtures with different proportions of the tautomeric compounds are meant.

It has furthermore been found that the new pyrazolin-5-one derivatives of the general formula (I)

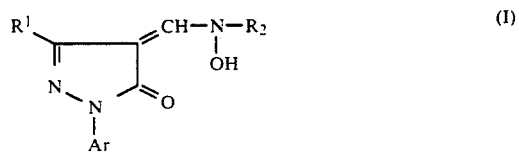

in which
$R^1$ represents alkyl, cycloalkyl, halogenoalkyl, in each case optionally substituted alkenyl or alkynyl, optionally substituted phenyl being selected as the substituent, halogenoalkenyl, alkoxy, alkoxyalkyl, alkylthioalkyl,alkylsulphonylalkyl,alkyl sulphinylalkyl, alkoxycarbonylalkyl, in each case optionally substituted aryl, aralkyl, aryloxyalkyl or arylthioalkyl, optionally substituted heterocyclyl, optionally substituted heterocyclylalkyl or the —NH—CO—$R^3$ or —CO—O—$R^4$ groups, in which $R^3$ and $R^4$ in each case independently of one another represent alkyl or aryl, $R^2$ represents hydrogen, alkyl, cycloalkyl, halogenoalkyl, alkyl, alkenyl, alkynyl, halogenoalkenyl, alkoxyalkyl, alkylthioalkyl, alkylsulphonylalkyl, alkylsulphinylalkyl or alkoxycarbonylalkyl and Ar represents optionally substituted aryl or a heterocyclyl which is optionally substituted and/or optionally fused, excluding the compounds 1-(3-chlorophenyl)-3-methylthiomethyl-4-(N-hydroxyaminomethylidene)-pyrazolin-5-one, 1-(4-chlorophenyl)-3-methylthiomethyl-4-(N-hydroxyaminomethylidene)-pyrazolin-5-one, 1-(4-trifluoromethylphenyl)-3-methylthiomethyl-4-(N-hydroxyaminomethylidene)-pyrazolin-5-one and 1-(4-nitrophenyl)-3-methylthiomethyl-4-(N-hydroxyaminomethylidene)-pyrazolin-5-one, are obtained when dimethylaminomethylidenepyrazolin-5-one derivatives of the formula (II)

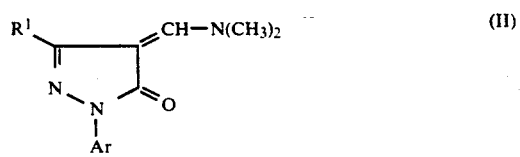

in which $R^1$ and Ar have the abovementioned meanings, are reacted with hydroxylamine hydrochloride derivatives of the formula (III)

$R^2$—NHOH × HX        (III)

in which $R^2$ has the abovementioned meaning and

HX represents an equivalent of a mineral acid, such as, for example, hydrochloric acid or a carboxylic acid, such as, for example, oxalic acid, if appropriate in the presence of a diluent.

Finally, it has been found that the new pyrazolin-5-one derivatives of the general formula (I) have excellent herbicidal properties.

Preferred compounds of the formula (I) are those in which $R^1$ represents straight-chain or branched alkyl having 1 to 8 carbon atoms, cycloalkyl having 3 to 7 carbon atoms, straight-chain or branched halogenoalkyl having 1 to 4 carbon atoms and 1 to 9 identical or different halogen atoms, in each case straight-chain or branched and in each case optionally monosubstituted to polysubstituted alkenyl or alkynyl in each case having 2 to 6 carbon atoms, suitable substituents being phenyl which is unsubstituted, or monosubstituted to polysubstituted by identical or different substituents, and the aryl substituents shown under Ar being mentioned as phenyl substituents; $R^1$ furthermore represents straight-chain or branched halogenoalkenyl having 2 to 4 carbon atoms and 1 to 7 identical or different halogen atoms, straight-chain or branched alkoxy having 1 to 4 carbon atoms, straight-chain or branched alkoxyalkyl in each case having 1 to 8 carbon atoms in the alkoxy and alkyl moiety, in each case straight-chain or branched alkylthioalkyl, alkylsulphonylalkyl or alkylsulphinylalkyl in each case having 1 to 4 carbon atoms in the individual alkyl moieties, straight-chain or branched alkoxycarbonylalkyl in each case having 1 to 4 carbon atoms in the alkoxy and alkyl moiety, phenyl or naphthyl which is in each case optionally monosubstituted to polysubstituted by identical or different substituents, phenylalkyl or naphthylalkyl in each case having 1 to 8 carbon atoms in the straight-chain or branched alkyl moiety and in each case optionally monosubstituted to polysubstituted in the aryl moiety by identical or different substituents, phenoxyalkyl or phenylthioalkyl in each case having 1 to 4 carbon atoms in the straight-chain or branched alkyl moiety and in each case optionally monosubstituted or disubstituted in the phenyl moiety, the aryl substituents shown under Ar in each case being mentioned as phenyl and naphthyl substituents; $R^1$ furthermore represents furyl, thienyl, pyrrolyl, pyridinyl, furylalkyl, thienylalkyl or pyrrolylalkyl in each case optionally having 1 to 8 carbon atoms in the straight-chain or branched alkyl moiety and in each case optionally monosubstituted to polysubstituted in the heterocyclyl moiety by identical or different substituents, suitable heterocyclyl substituents being the aryl substituents shown under Ar; $R^1$ furthermore represents the —$NHCOR^3$ or —$COOR^4$ groups, in which $R^3$ and $R^4$ in each case independently of one another represent straight-chain or branched alkyl having 1 to 4 carbon atoms or phenyl, $R^2$ represents hydrogen, straight-chain or branched alkyl having 1 to 8 carbon atoms, cycloalkyl having 3 to 7 carbon atoms, straight-chain or branched halogenoalkyl having 1 to 8 carbon atoms and 1 to 17 identical or different halogen atoms, in each case straight-chain or branched alkenyl or alkynyl in each case having 2 to 6 carbon atoms, straight-chain or branched halogenoalkenyl having 2 to 4 carbon atoms and 1 to 9 identical or different halogen atoms, straight-chain or branched alkoxyalkyl in each case having 1 to 4 carbon atoms in the alkoxy and alkyl moiety in each case straight-chain or branched alkylthioalkyl, alkylsulphonylalkyl or alkylsulphinylalkyl in each case having 1 to 4 carbon atoms in the individual alkyl moieties, and straight-chain or branched alkoxycarbonylalkyl in each case having 1 to 4 carbon atoms in the alkoxy and alkyl moiety, and Ar represents phenyl or naphthyl which is in each case optionally monosubstituted to polysubstituted by identical or different substituents, suitable substituents being: halogen, nitro, cyano, carboxyl, in each case straight-chain or branched alkyl, alkoxy or alkylthio in each case having 1 to 6 carbon atoms, straight-chain or branched cyanoalkyl having 1 to 6 carbon atoms, straight-chain or branched alkoxycarbonyl having 1 to 6 carbon atoms in the alkoxy moiety, straight-chain or branched alkynyloxy having 2 to 6 carbon atoms, in each case straight-chain or branched halogenoalkyl, halogenoalkoxy or halogenoalkylthio in each case having 1 to 6 carbon atoms and in each case 1 to 13 identical or different halogen atoms, straight-chain or branched alkylsulphonyl having 1 to 6 carbon atoms, straight-chain or branched halogenoalkylsulphonyl having 1 to 6 carbon atoms and 1 to 13 identical or different halogen atoms, dialkylamino having 1 to 6 carbon atoms in the respective straight-chain or branched alkyl moieties, phenyl, naphthyl, phenoxy or naphthoxy which is in each case optionally monosubstituted to polysubstituted by identical or different substituents, phenylalkyl or naphthylalkyl in each case having 1 to 6 carbon atoms in the straight-chain or branched alkyl moiety and in each case optionally monosubstituted to polysubstituted by identical or different substituents; Ar furthermore represents furyl, thienyl, pyrrolyl or pyridyl which is in each case optionally monosubstituted to polysubstituted by identical or different substituents and in each case optionally fused to a benzene ring, suitable substituents in each case being the abovementioned aryl substituents, excluding the abovementioned compounds.

Particularly preferred compounds of the formula (I) are those in which $R^1$ represents straight-chain or branched alkyl having 1 to 6 carbon atoms, cycloalkyl having 3 to 6 carbon atoms, halogenoalkyl having 1 or 2 carbon atoms, and 1 to 5 fluorine and/or chlorine atoms, in each case straight-chain or branched and in each case optionally monosubstituted or disubstituted alkenyl or alkynyl in each case having 2 to 4 carbon atoms, suitable substituents being phenyl which is unsubstituted, or monosubstituted or disubstituted by identical or different substituents and the aryl substituents shown under Ar being mentioned as phenyl substituents; $R^1$ furthermore represents halogenoalkenyl having 2 or 3 carbon atoms and 1 to 5 fluorine and/or chlorine atoms, alkoxy having 1 or 2 carbon atoms, straight-chain or branched alkoxyalkyl in each case having 1 to 6 carbon atoms in the alkoxy and alkyl moiety, alkylthioalkyl, alkylsulphonylalkyl or alkylsulphinylalkyl in each case having 1 or 2 carbon atoms in the individual alkyl moieties, alkoxycarbonylalkyl in each case having 1 or 2 carbon atoms in the alkoxy and alkyl moiety phenyl or naphthyl which is in each case optionally monosubstituted to pentasubstituted by identical or different substituents, phenylalkyl or naphthylalkyl in each case having 1 to 6 carbon atoms in the straight-chain or branched alkyl moiety and in each case optionally monosubstituted to pentasubstituted in the aryl moiety by identical or different substituents, the aryl substituents shown under Ar being mentioned in each case as phenyl and naphthyl substituents; $R^1$ furthermore represents phenoxyalkyl or phenylthioalkyl in each case having 1 or 2 carbon atoms in the alkyl moiety, furyl, thienyl, pyrrolyl or pyridinyl which is in each case monosubstituted to trisubstituted by identical or different substituents, furylalkyl, thienylalkyl or pyrrolylalkyl in each case having 1 to 6 carbon atoms in the straight-chain or branched alkyl moiety and in each case monosubstituted to trisubstituted in the heterocyclyl moiety by identical or different substituents, suitable heterocyclyl substituents in each case being the aryl substituents shown under Ar; $R^1$ furthermore represents the —NHCOR$^3$ or —COOR$^4$ groups in which $R^3$ and $R^4$ in each case independently of one another represent methyl, ethyl or phenyl, $R^2$ represents hydrogen, straight-chain or branched alkyl having 1 to 6 carbon atoms, cycloalkyl having 3 to 6 carbon atoms, straight-chain or branched halogenoalkyl having 1 to 6 carbon atoms and 1 to 13 fluorine and/or chlorine atoms, in each case straight-chain or branched alkenyl or alkynyl having 2 to 4 carbon atoms, halogeno alkenyl having 2 or 3 carbon atoms and 1 to 5 fluorine and/or chlorine atoms, alkoxyalkyl in each case having 1 or 2 carbon atoms in the alkoxy and alkyl moiety, alkylthioalkyl, alkylsulphonylalkyl or alkylsulphinylalkyl in each case having 1 or 2 carbon atoms in the individual alkyl moieties, and alkoxycarbonylalkyl in each case having 1, or 2 carbon atoms in the alkoxy and alkyl moiety and Ar represents phenyl or naphthyl which is in each case optionally monosubstituted to pentasubstituted, preferably monosubstituted to trisubstituted, in particular monosubstituted, by identical or different substituents, suitable substituents being: fluorine, chlorine, bromine, nitro, cyano, carboxyl, in each case straight-chain or branched alkyl, alkoxy or alkylthio in each case having 1 to 4 carbon atoms, straight-chain or branched cyanoalkyl having 1 to 4 carbon atoms, straight-chain or branched alkoxycarbonyl having 1 to 4 carbon atoms in the alkoxy moiety, straight-chain or branched alkynyloxy having 2 to 4 carbon atoms, in each case straight-chain or branched halogenoalkyl, halogenoalkoxy or halogenoalkylthio in each case having 1 to 4 carbon atoms and in each case 1 to 9 identical or different halogen atoms, straight-chain or branched alkylsulphonyl having 1 to 4 carbon atoms, straight-chain or branched halogenoalkylsulphonyl having 1 to 4 carbon atoms and 1 to 9 identical or different halogen atoms, dialkylamino having 1 to 4 carbon atoms in the respective straight-chain or branched alkyl moieties, phenyl, naphthyl, phenoxy or naphthoxy which is in each case optionally monosubstituted or disubstituted by identical or different substituents, phenylalkyl or naphthylalkyl in each case having 1 to 4 carbon atoms in the straight-chain or branched alkyl moiety and in each case optionally monosubstituted or disubstituted by identical or different substituents; Ar furthermore represents furyl, thienyl, pyrrolyl or pyridyl which is in each case optionally monosubstituted or disubstituted by identical or different substituents, suitable substituents in each case being the abovementioned aryl substituents, excluding the abovementioned compounds.

Very particularly preferred compounds of the formula (I) are those in which $R^1$ represents methyl, ethyl, n-propyl, i-propyl, n-butyl, i-butyl, s-butyl, t-butyl, 2-phenylvinyl, 2-(3-trifluoromethylphenyl)-vinyl, methoxymethyl, methoxyethyl, ethoxymethyl, ethoxyethyl, phenyl or naphthyl which is optionally monosubstituted to trisubstituted by identical or different substituents, phenylmethyl or phenylethyl which is in each case optionally monosubstituted to trisubstituted in the phenyl moiety, the aryl substituents shown under Ar, in particular fluorine, chlorine, bromine, nitro, cyano, methyl, ethyl, methoxy, ethoxy, trifluoromethyl, trifluoromethoxy and trifluoromethylthio being mentioned as phenyl and naphthyl substituents; $R^1$ furthermore represents furyl, thienyl, pyridyl, furylmethyl, thienylmethyl or pyridylmethyl, $R^2$ represents hydrogen, methyl, ethyl, n-propyl, i-propyl, n-butyl, i-butyl, s-butyl, t-butyl, trifluoromethyl, trichloromethyl, 2,2,2-trifluoroethyl, 2,2,2-trichloroethyl, vinyl, allyl, 1-propenyl, ethynyl, 1-propynyl, 2-propynyl, 2-fluorovinyl, methoxymethyl or methylthiomethyl and Ar represents phenyl which is in each case optionally monosubstituted to trisubstituted, in particular monosubstituted, by identical or different substituents, suitable substituents being: fluorine, chlorine, bromine, nitro, cyano, carboxyl, methyl, ethyl, methoxy, ethoxy, methylthio, ethylthio, cyanomethyl, 1-cyanoethyl, 2-cyanoethyl, methoxycarbonyl, ethynyloxy, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-chloroethyl, 2,2-dichloroethyl, 2,2,2-trichloroethyl, fluoromethoxy, difluoromethoxy, trifluoromethoxy, chloromethoxy, dichloromethoxy, trichloromethoxy, fluoromethylthio, difluoromethylthio, trifluoromethylthio, chloromethylthio, dichloromethylthio, trichloromethylthio, methylsulphonyl, ethylsulphonyl, fluoromethylsulphonyl, difluoromethylsulphonyl, trifluoromethylsulphonyl, chloromethylsulphonyl, dichloromethylsulphonyl, trichloromethylsulphonyl, dimethylamino, diethylamino, phenyl, phenoxy, phenylmethyl or phenylethyl.

$R^1$ in particular represents methyl, ethyl, n- or i-propyl, methoxymethyl, unsubstituted phenyl or phenyl or phenylmethyl which is in each case monosubstituted to trisubstituted, in particular monosubstituted, by identical or different substituents from the series comprising fluorine, chlorine, bromine, nitro, methyl, methoxy, trifluoromethyl, trifluoromethoxy and trifluoromethylthio.

$R^2$ in particular represents methyl, and

Ar in particular represents unsubstituted phenyl or phenyl which is monosubstituted or disubstituted by fluorine, chlorine, cyano, nitro, methyl, methoxy, trifluoromethyl, trifluoromethoxy, trifluoromethyl thio or methylsulphonyl.

The substitution of the phenyl ring in Ar takes place, preferably, in the para-position. The phenyl ring is preferably substituted by fluorine.

In particular, the following pyrazolin-5-one derivatives of the formula (I)

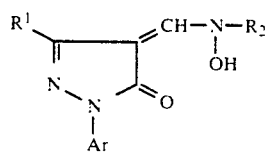
(I)
may be mentioned by way of example in addition to the compounds mentioned in the Preparation Examples:
TABLE 1
| R¹ | R² | Ar |
|---|---|---|
| $-C_3H_7$-n | $CH_3$ | phenyl |
| $-C_3H_7$-n | $CH_3$ | 2-F-phenyl |
| $-C_3H_7$-n | $CH_3$ | 3-F-phenyl |
| $-C_3H_7$-n | $CH_3$ | 4-Cl-phenyl |
| $-C_3H_7$-n | $CH_3$ | 4-Br-phenyl |
| $-C_3H_7$-n | $CH_3$ | 4-$CF_3$-phenyl |
| $-C_3H_7$-n | $CH_3$ | 4-$CH_3$-phenyl |
| $-C_3H_7$-n | $CH_3$ | 4-$OCH_3$-phenyl |
| $-C_3H_7$-n | $CH_3$ | 4-$SCF_3$-phenyl |
| $-C_3H_7$-n | $CH_3$ | 4-CN-phenyl |
| $-C_3H_7$-n | $CH_3$ | 4-$OCF_3$-phenyl |

-continued
| | | |
|---|---|---|
| —C$_3$H$_7$-n | CH$_3$ | 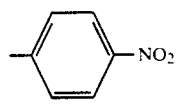 |
| —C$_3$H$_7$-n | CH$_3$ | 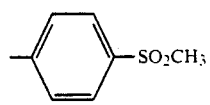 |
| —C$_3$H$_7$-n | CH$_3$ | 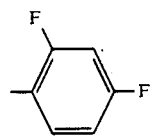 |
| —C$_3$H$_7$-n | CH$_3$ | 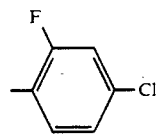 |
| —CH$_2$OCH$_3$ | CH$_3$ | 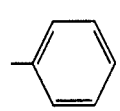 |
| —CH$_2$OCH$_3$ | CH$_3$ | 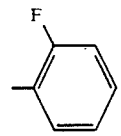 |
| —CH$_2$OCH$_3$ | CH$_3$ | 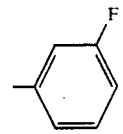 |
| —CH$_2$OCH$_3$ | CH$_3$ |  |
| —CH$_2$OCH$_3$ | CH$_3$ | 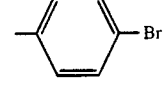 |
| —CH$_2$OCH$_3$ | CH$_3$ | 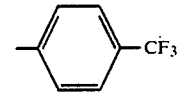 |
| —CH$_2$OCH$_3$ | CH$_3$ | 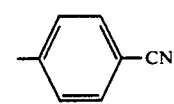 |
| —CH$_2$OCH$_3$ | CH$_3$ | 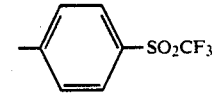 |
| —CH$_2$OCH$_3$ | CH$_3$ | 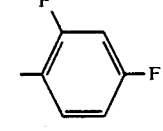 |

-continued
| | | |
|---|---|---|
| —C$_4$H$_9$-n | CH$_3$ | 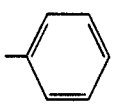 |
| —C$_4$H$_9$-n | CH$_3$ | 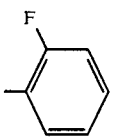 |
| —C$_4$H$_9$-n | CH$_3$ | 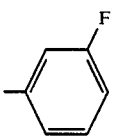 |
| —C$_4$H$_9$-n | CH$_3$ | 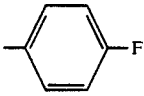 |
| —C$_4$H$_9$-n | CH$_3$ | 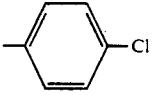 |
| —C$_4$H$_9$-n | CH$_3$ |  |
| —C$_4$H$_9$-n | CH$_3$ | 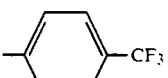 |
| —C$_4$H$_9$-n | CH$_3$ | 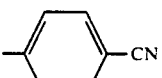 |
| —C$_4$H$_9$-n | CH$_3$ | 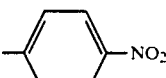 |
| —C$_4$H$_9$-n | CH$_3$ | 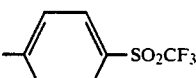 |
| —C$_4$H$_9$-n | CH$_3$ | 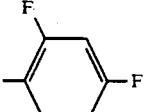 |
| —CH$_2$—CH(CH$_3$)$_2$ | CH$_3$ | 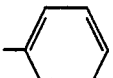 |
| —CH$_2$—CH(CH$_3$)$_2$ | CH$_3$ | 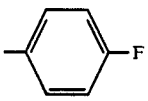 |

-continued
| | | |
|---|---|---|
| —CH₂—CH(CH₃)₂ | CH₃ | 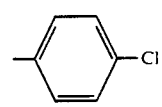 |
| —CH₂—CH(CH₃)₂ | CH₃ | 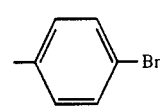 |
| —CH₂—CH(CH₃)₂ | CH₃ | 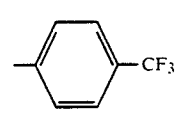 |
| —CH₂—CH(CH₃)₂ | CH₃ | 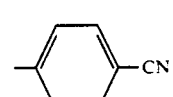 |
| —CH₂—CH(CH₃)₂ | CH₃ | 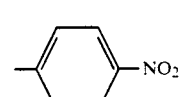 |
| —CH₂—CH(CH₃)₂ | CH₃ | 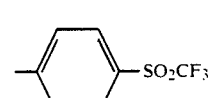 |
| —CH₂—CH(CH₃)₂ | CH₃ | 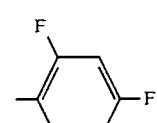 |
| —CH₂—CH(CH₃)₂ | CH₃ | 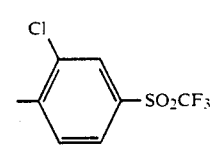 |
|  | CH₃ | 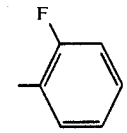 |
|  | CH₃ | 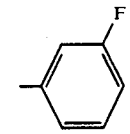 |
|  | CH₃ | 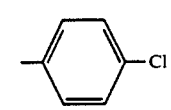 |
|  | CH₃ | 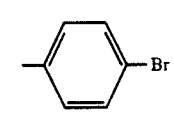 |
|  | CH₃ | 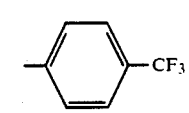 |

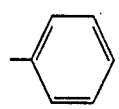 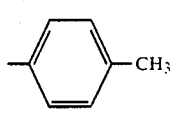
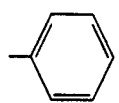 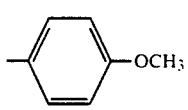
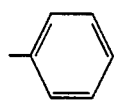 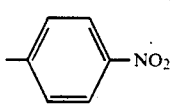
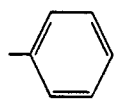 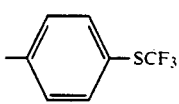
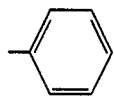 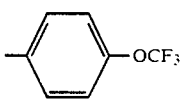
 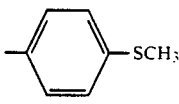
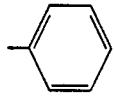 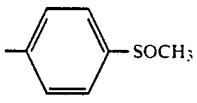
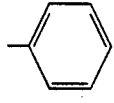 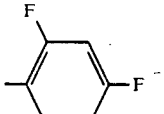
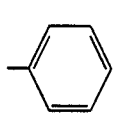 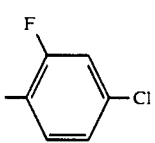
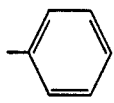 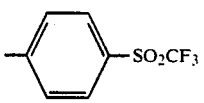
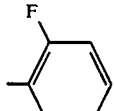 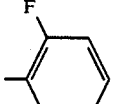
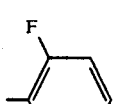 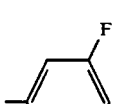
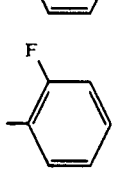 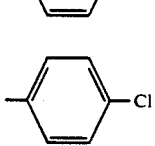

-continued
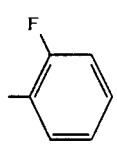 CH₃ 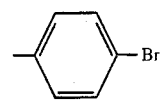
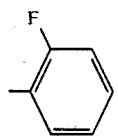 CH₃ 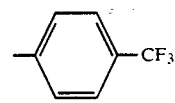
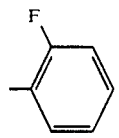 CH₃ 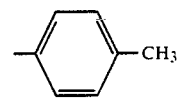
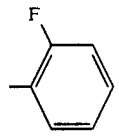 CH₃ 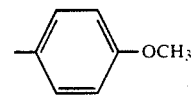
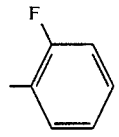 CH₃ 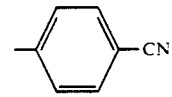
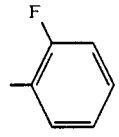 CH₃ 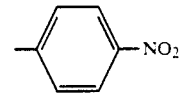
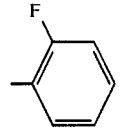 CH₃ 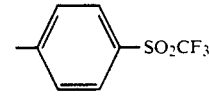
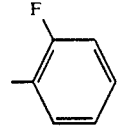 CH₃ 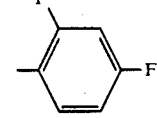
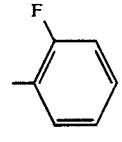 CH₃ 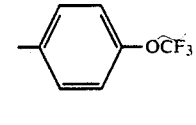
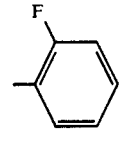 CH₃ 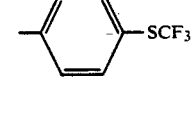
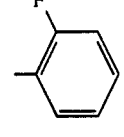 CH₃ 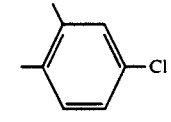

-continued
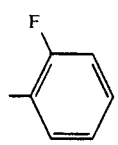 CH₃ 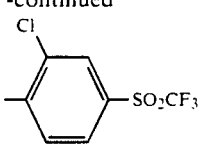
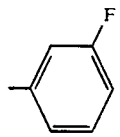 CH₃ 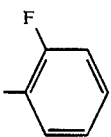
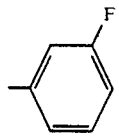 CH₃ 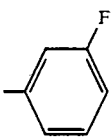
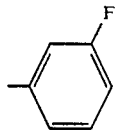 CH₃ 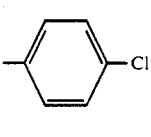
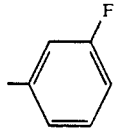 CH₃ 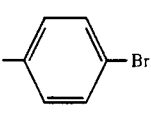
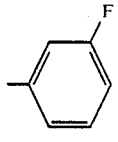 CH₃ 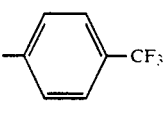
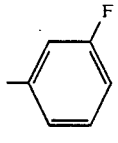 CH₃ 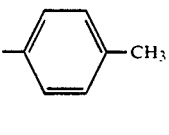
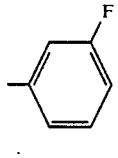 CH₃ 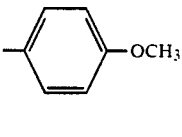
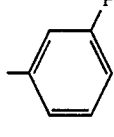 CH₃ 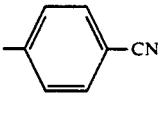
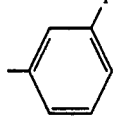 CH₃ 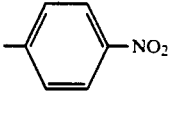
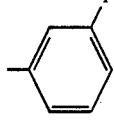 CH₃ 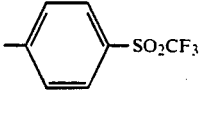

-continued
| | | |
|---|---|---|
| 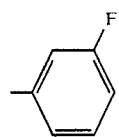 | CH₃ | 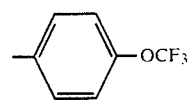 |
| 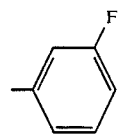 | CH₃ | 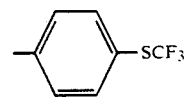 |
| 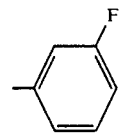 | CH₃ | 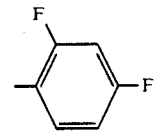 |
| 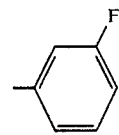 | CH₃ | 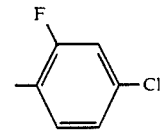 |
| 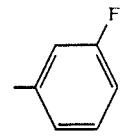 | CH₃ | 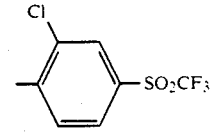 |
| 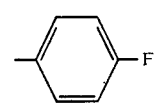 | CH₃ | 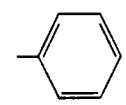 |
| 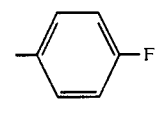 | CH₃ | 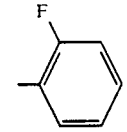 |
| 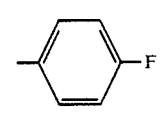 | CH₃ | 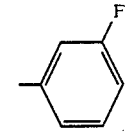 |
| 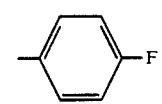 | CH₃ | 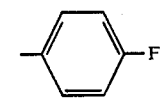 |
| 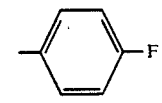 | CH₃ | 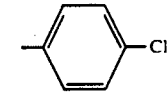 |
| 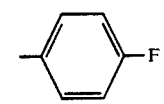 | CH₃ | 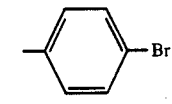 |
| 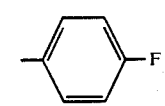 | CH₃ | 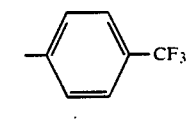 |

-continued
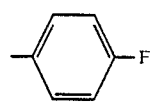 CH₃ 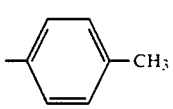 CH₃
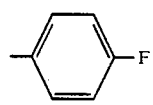 CH₃ 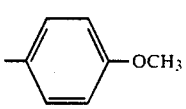 OCH₃
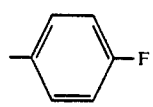 CH₃ 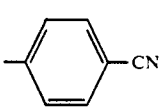 CN
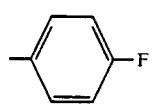 CH₃ 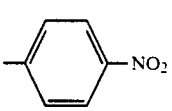 NO₂
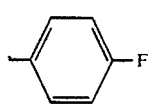 CH₃ 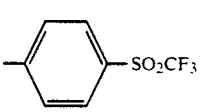 SO₂CF₃
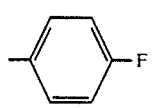 CH₃ 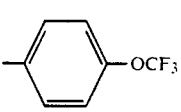 OCF₃
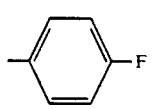 CH₃ 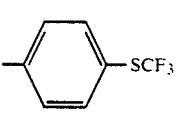 SCF₃
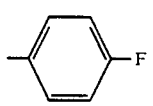 CH₃ 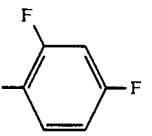
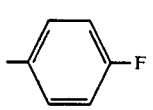 CH₃ 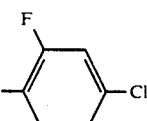
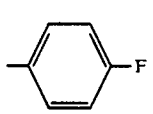 CH₃ 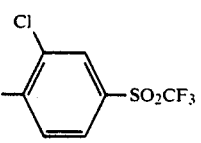
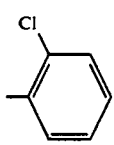 CH₃ 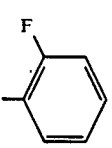
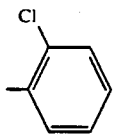 CH₃ 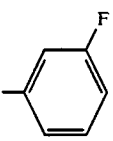

-continued

| | | |
|---|---|---|
| 2-Cl-C6H4- | CH3 | 4-Cl-C6H4- |
| 2-Cl-C6H4- | CH3 | 4-Br-C6H4- |
| 2-Cl-C6H4- | CH3 | 4-CF3-C6H4- |
| 2-Cl-C6H4- | CH3 | 4-CH3-C6H4- |
| 2-Cl-C6H4- | CH3 | 4-OCH3-C6H4- |
| 2-Cl-C6H4- | CH3 | 4-CN-C6H4- |
| 2-Cl-C6H4- | CH3 | 4-NO2-C6H4- |
| 2-Cl-C6H4- | CH3 | 4-SO2CF3-C6H4- |
| 2-Cl-C6H4- | CH3 | 4-OCF3-C6H4- |
| 2-Cl-C6H4- | CH3 | 4-SCF3-C6H4- |
| 2-Cl-C6H4- | CH3 | 2,4-F2-C6H3- |

-continued
| | | |
|---|---|---|
| 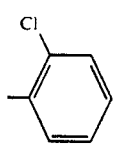 | CH₃ | 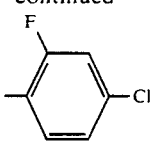 (F, Cl) |
| 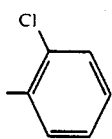 | CH₃ | 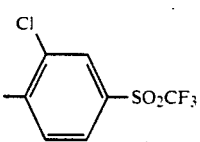 (Cl, SO₂CF₃) |
| 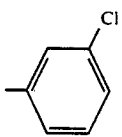 | CH₃ | 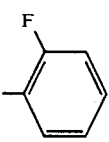 (F) |
| 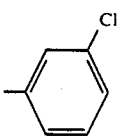 | CH₃ | 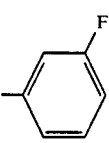 (F) |
| 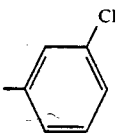 | CH₃ | 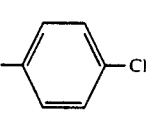 (Cl) |
| 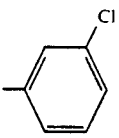 | CH₃ | 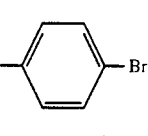 (Br) |
| 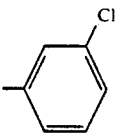 | CH₃ | 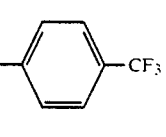 (CF₃) |
| 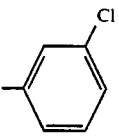 | CH₃ | 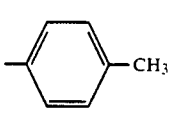 (CH₃) |
| 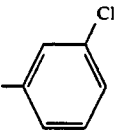 | CH₃ | 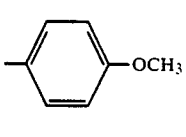 (OCH₃) |
| 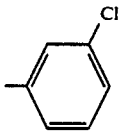 | CH₃ | 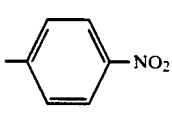 (NO₂) |
| 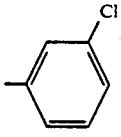 | CH₃ | 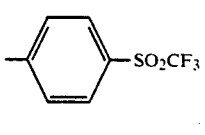 (SO₂CF₃) |

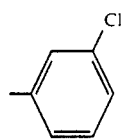 CH3 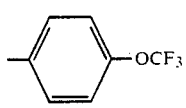
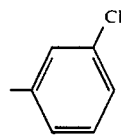 CH3 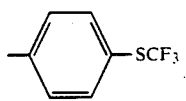
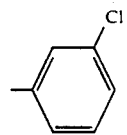 CH3 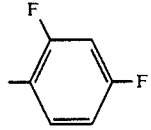
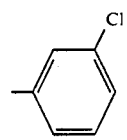 CH3 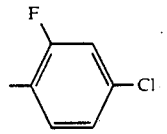
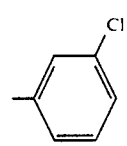 CH3 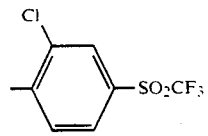
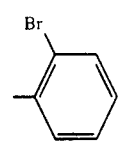 CH3 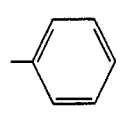
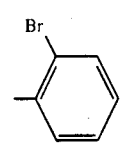 CH3 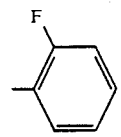
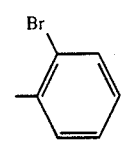 CH3 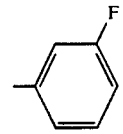
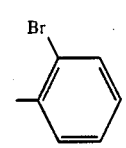 CH3 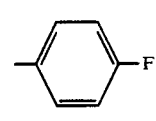
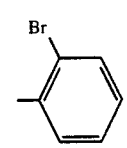 CH3 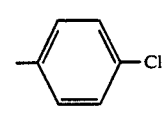
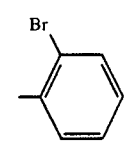 CH3 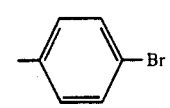

-continued
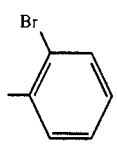 CH₃ 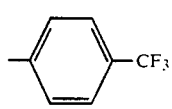
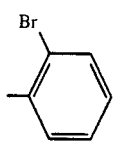 CH₃ 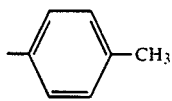
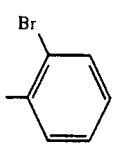 CH₃ 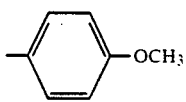
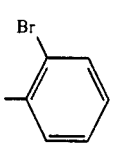 CH₃ 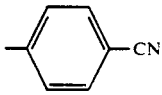
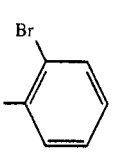 CH₃ 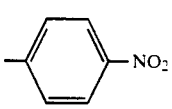
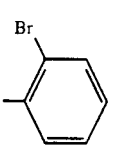 CH₃ 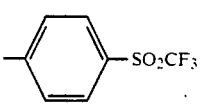
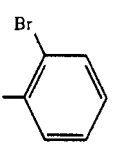 CH₃ 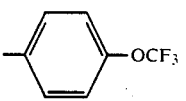
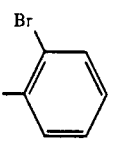 CH₃ 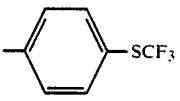
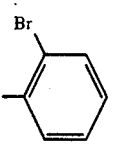 CH₃ 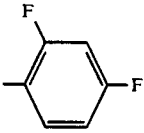
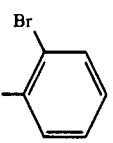 CH₃ 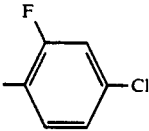
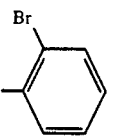 CH₃ 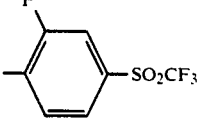

-continued
| | | |
|---|---|---|
| 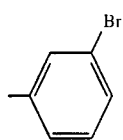 | CH₃ | 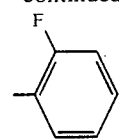 |
| 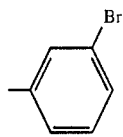 | CH₃ | 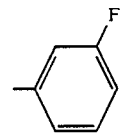 |
| 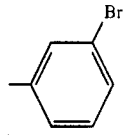 | CH₃ | 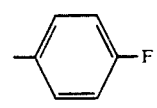 |
| 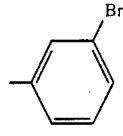 | CH₃ | 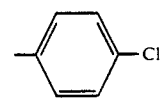 |
| 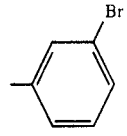 | CH₃ | 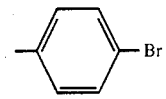 |
| 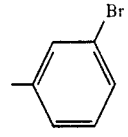 | CH₃ | 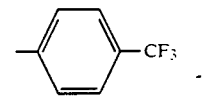 |
| 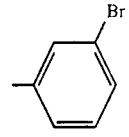 | CH₃ | 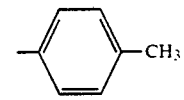 |
| 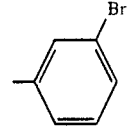 | CH₃ | 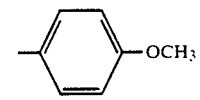 |
| 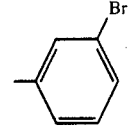 | CH₃ | 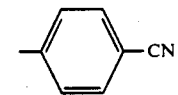 |
| 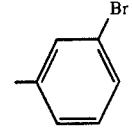 | CH₃ | 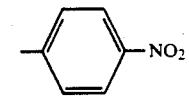 |
| 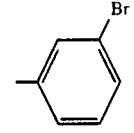 | CH₃ | 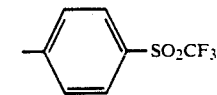 |

-continued
| | | |
|---|---|---|
| 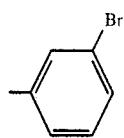 | CH₃ | 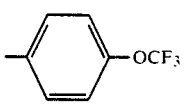 |
| 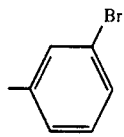 | CH₃ | 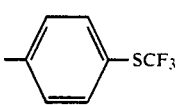 |
| 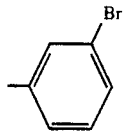 | CH₃ | 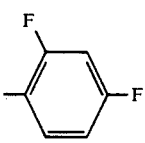 |
| 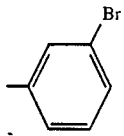 | CH₃ | 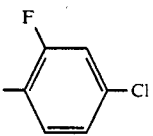 |
| 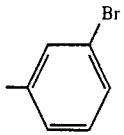 | CH₃ | 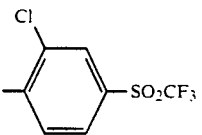 |
| 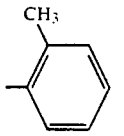 | CH₃ | 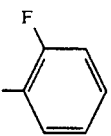 |
| 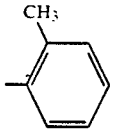 | CH₃ | 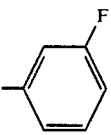 |
| 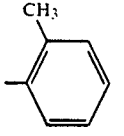 | CH₃ | 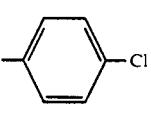 |
| 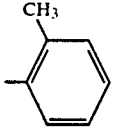 | CH₃ | 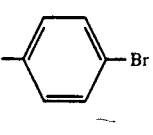 |
| 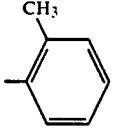 | CH₃ | 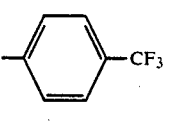 |
| 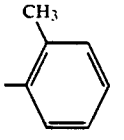 | CH₃ | 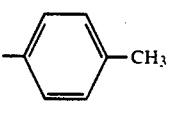 |

-continued
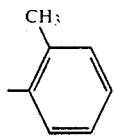 CH₃ 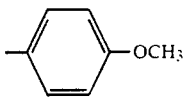
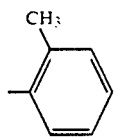 CH₃ 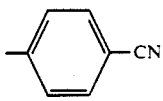
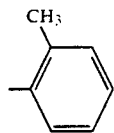 CH₃ 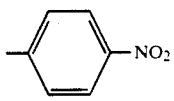
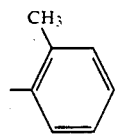 CH₃ 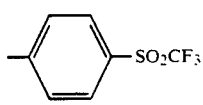
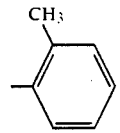 CH₃ 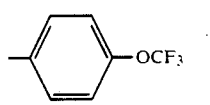
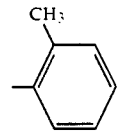 CH₃ 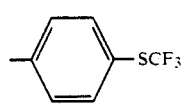
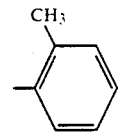 CH₃ 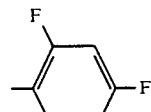
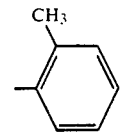 CH₃ 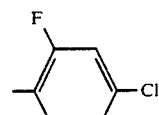
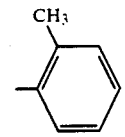 CH₃ 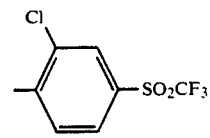
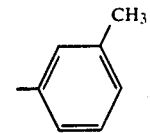 CH₃ 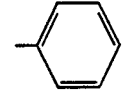
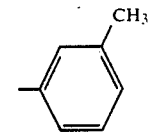 CH₃ 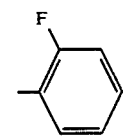

-continued

| | | |
|---|---|---|
| 3-CH₃-C₆H₄- | CH₃ | 2-F-C₆H₄- |
| 3-CH₃-C₆H₄- | CH₃ | 4-F-C₆H₄- |
| 3-CH₃-C₆H₄- | CH₃ | 4-Cl-C₆H₄- |
| 3-CH₃-C₆H₄- | CH₃ | 4-Br-C₆H₄- |
| 3-CH₃-C₆H₄- | CH₃ | 4-CF₃-C₆H₄- |
| 3-CH₃-C₆H₄- | CH₃ | 4-CH₃-C₆H₄- |
| 3-CH₃-C₆H₄- | CH₃ | 4-OCH₃-C₆H₄- |
| 3-CH₃-C₆H₄- | CH₃ | 4-CN-C₆H₄- |
| 3-CH₃-C₆H₄- | CH₃ | 4-NO₂-C₆H₄- |
| 3-CH₃-C₆H₄- | CH₃ | 4-SO₂CF₃-C₆H₄- |
| 3-CH₃-C₆H₄- | CH₃ | 4-OCF₃-C₆H₄- |

-continued
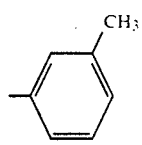 CH₃ 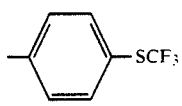
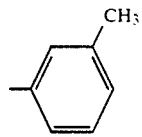 CH₃ 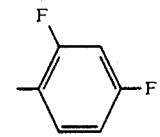
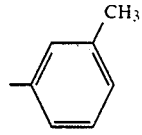 CH₃ 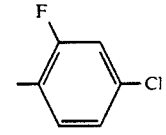
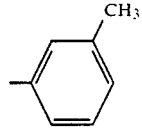 CH₃ 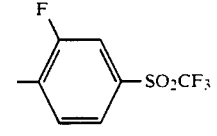
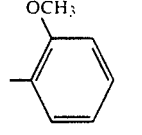 CH₃ 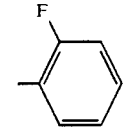
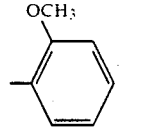 CH₃ 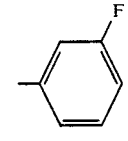
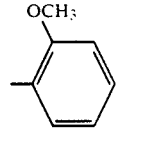 CH₃ 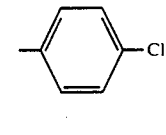
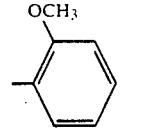 CH₃ 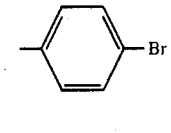
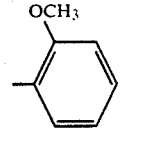 CH₃ 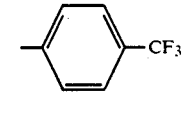
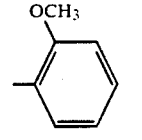 CH₃ 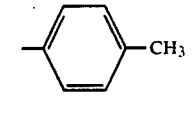
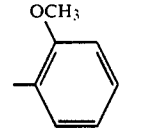 CH₃ 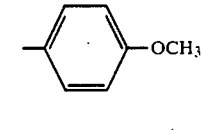

-continued
| | | |
|---|---|---|
| 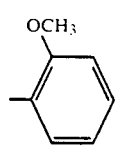 | CH₃ | 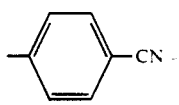 |
| 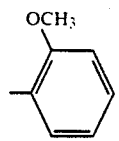 | CH₃ | 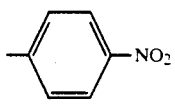 |
| 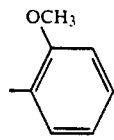 | CH₃ | 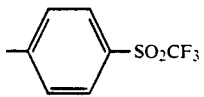 |
| 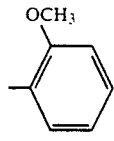 | CH₃ | 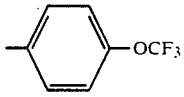 |
| 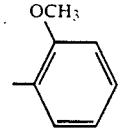 | CH₃ | 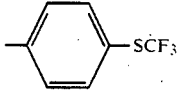 |
| 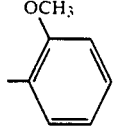 | CH₃ | 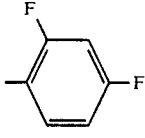 |
| 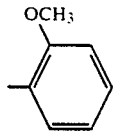 | CH₃ | 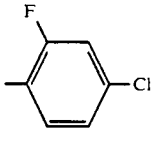 |
| 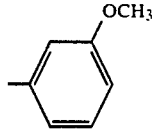 | CH₃ | 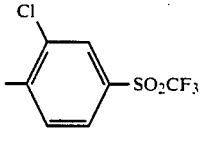 |
| 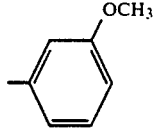 | CH₃ | 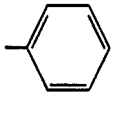 |
| 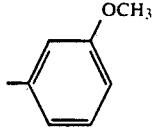 | CH₃ | 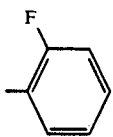 |
| | | 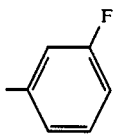 |

-continued
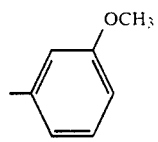 CH₃ 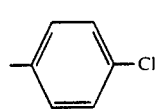
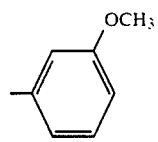 CH₃ 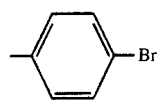
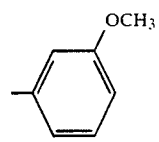 CH₃ 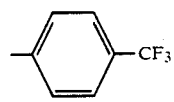
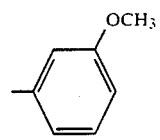 CH₃ 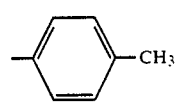
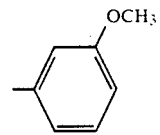 CH₃ 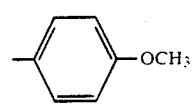
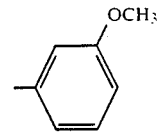 CH₃ 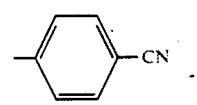
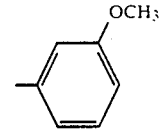 CH₃ 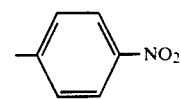
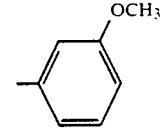 CH₃ 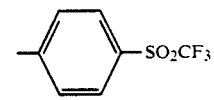
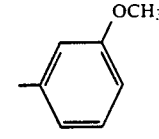 CH₃ 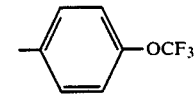
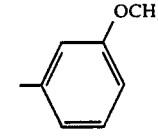 CH₃ 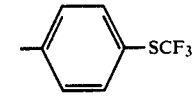
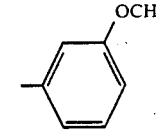 CH₃ 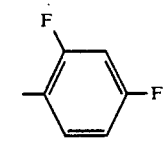

-continued
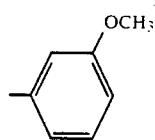 CH₃ 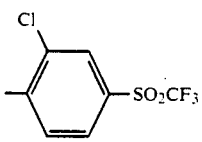
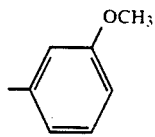 CH₃ 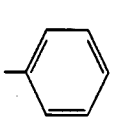
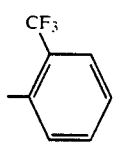 CH₃ 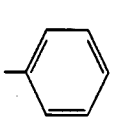
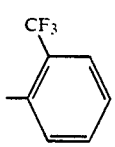 CH₃ 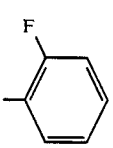
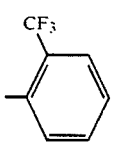 CH₃ 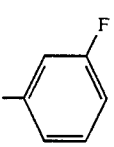
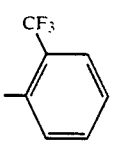 CH₃ 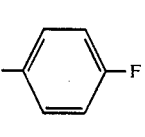
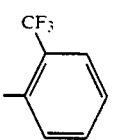 CH₃ 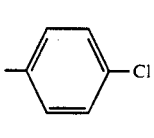
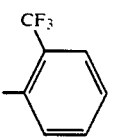 CH₃ 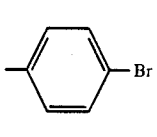
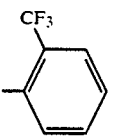 CH₃ 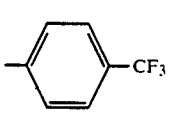
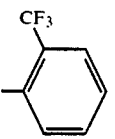 CH₃ 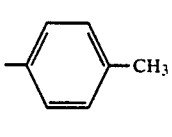
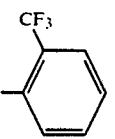 CH₃ 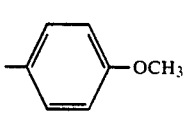

-continued
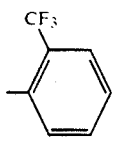 CH₃ 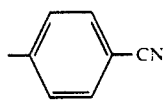
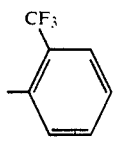 CH₃ 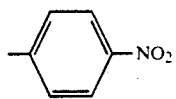
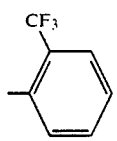 CH₃ 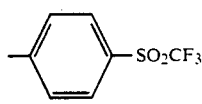
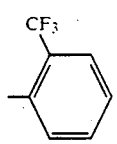 CH₃ 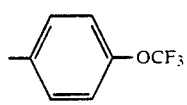
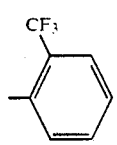 CH₃ 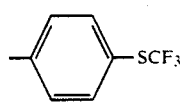
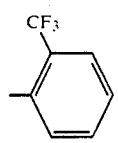 CH₃ 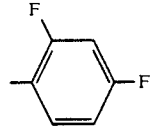
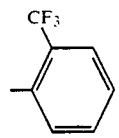 CH₃ 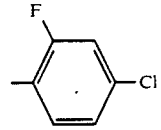
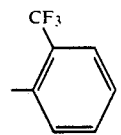 CH₃ 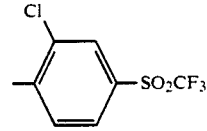
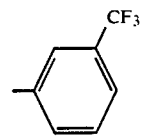 CH₃ 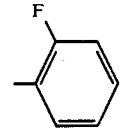
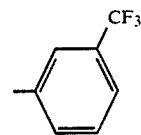 CH₃ 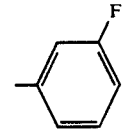
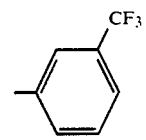 CH₃ 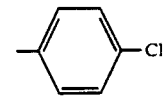

-continued
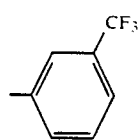 CH₃ 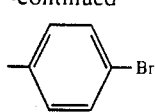
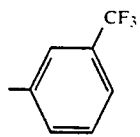 CH₃ 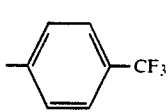
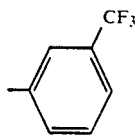 CH₃ 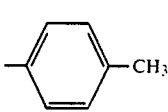
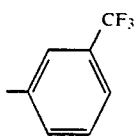 CH₃ 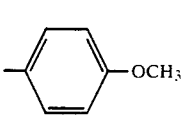
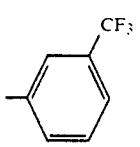 CH₃ 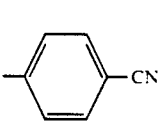
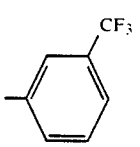 CH₃ 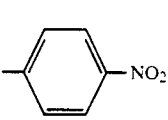
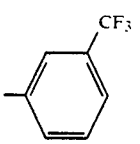 CH₃ 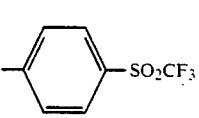
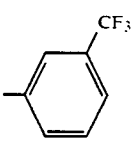 CH₃ 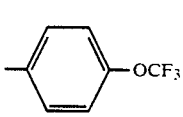
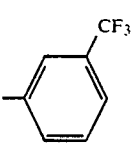 CH₃ 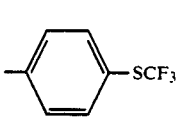
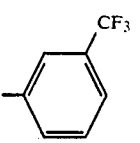 CH₃ 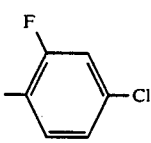
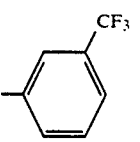 CH₃ 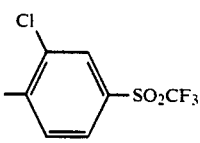

-continued
| | | |
|---|---|---|
| 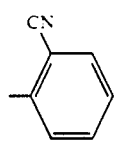 | CH₃ | 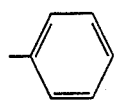 |
| 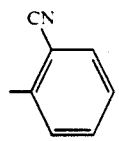 | CH₃ | 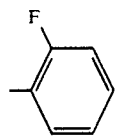 |
| 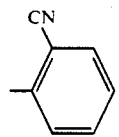 | CH₃ | 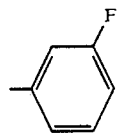 |
| 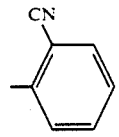 | CH₃ | 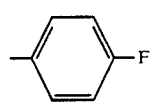 |
| 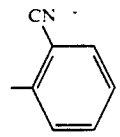 | CH₃ | 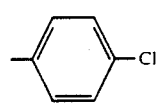 |
| 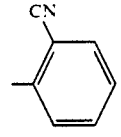 | CH₃ | 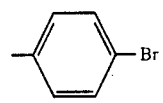 |
| 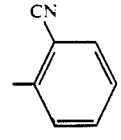 | CH₃ | 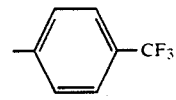 |
| 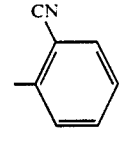 | CH₃ | 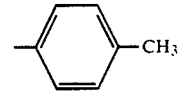 |
| 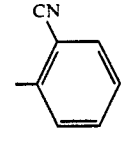 | CH₃ | 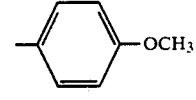 |
| 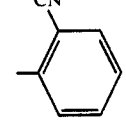 | CH₃ | 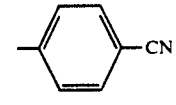 |
| 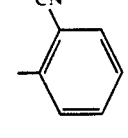 | CH₃ | 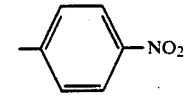 |

| | | |
|---|---|---|
| 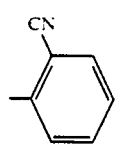 | CH₃ | 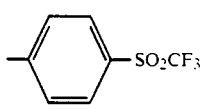 |
| 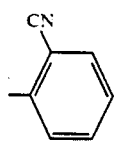 | CH₃ | 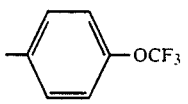 |
| 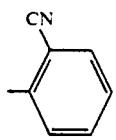 | CH₃ | 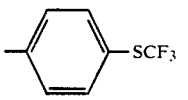 |
| 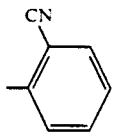 | CH₃ | 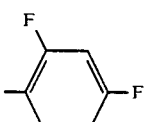 |
| 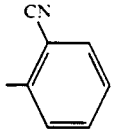 | CH₃ | 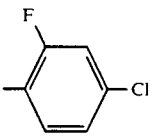 |
| 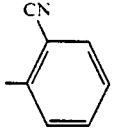 | CH₃ | 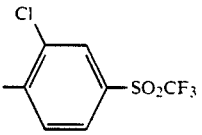 |
| 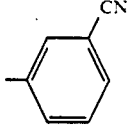 | CH₃ | 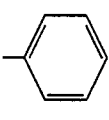 |
| 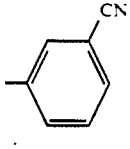 | CH₃ | 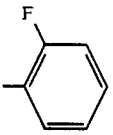 |
| 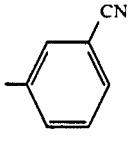 | CH₃ | 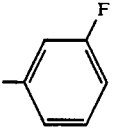 |
| 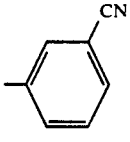 | CH₃ | 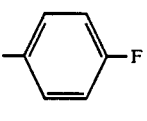 |
| 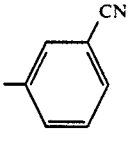 | CH₃ | 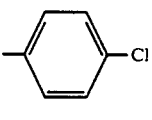 |

-continued
| | | |
|---|---|---|
| 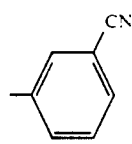 | CH₃ | 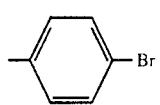 |
| 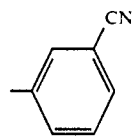 | CH₃ | 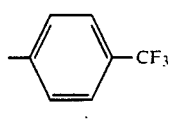 |
| 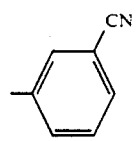 | CH₃ | 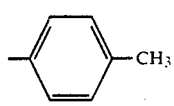 |
| 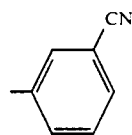 | CH₃ | 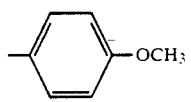 |
| 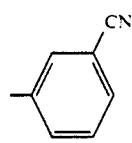 | CH₃ | 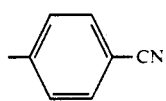 |
| 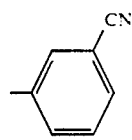 | CH₃ | 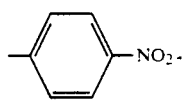 |
| 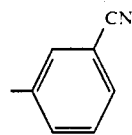 | CH₃ | 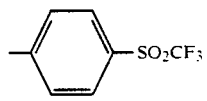 |
| 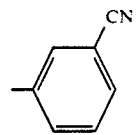 | CH₃ | 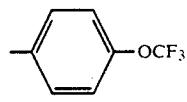 |
| 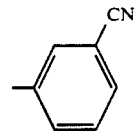 | CH₃ | 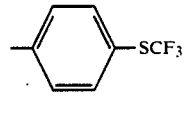 |
| 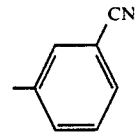 | CH₃ | 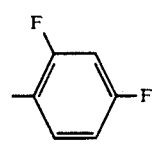 |
| 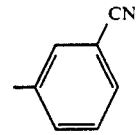 | CH₃ | 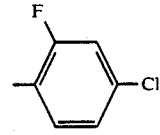 |

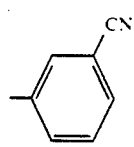 CH₃ 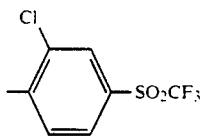
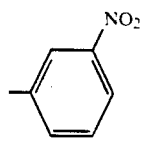 CH₃ 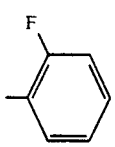
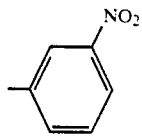 CH₃ 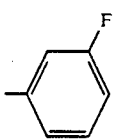
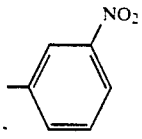 CH₃ 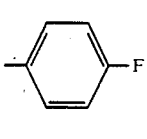
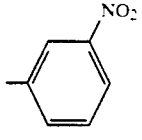 CH₃ 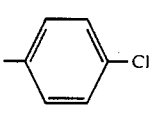
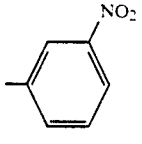 CH₃ 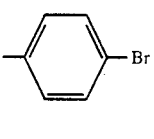
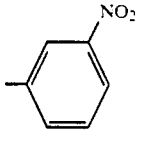 CH₃ 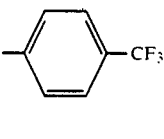
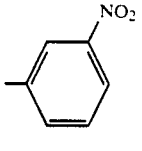 CH₃ 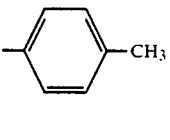
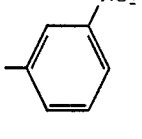 CH₃ 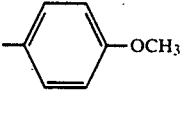
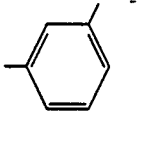 CH₃ 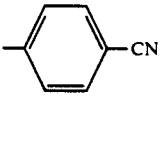
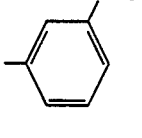 CH₃ 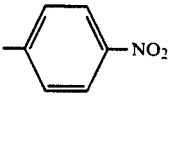

-continued
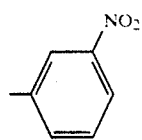 CH₃ 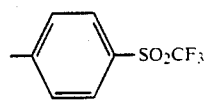
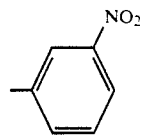 CH₃ 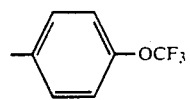
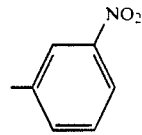 CH₃ 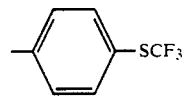
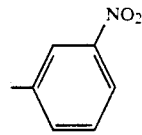 CH₃ 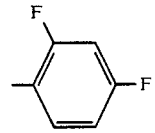
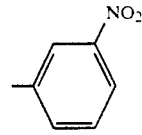 CH₃ 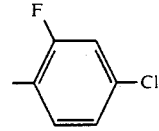
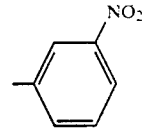 CH₃ 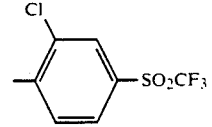
 CH₃ 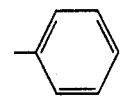
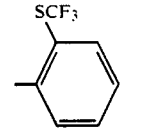 CH₃ 
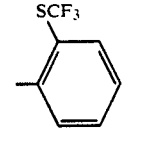 CH₃ 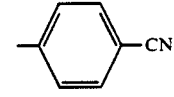
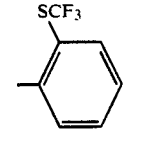 CH₃ 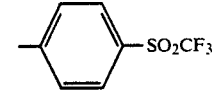
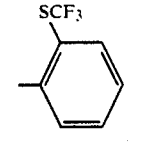 CH₃ 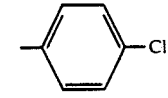

-continued
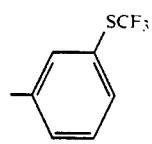 CH₃ 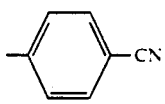
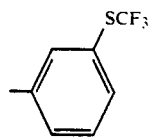 CH₃ 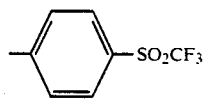
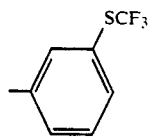 CH₃ 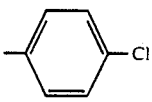
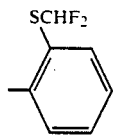 CH₃ 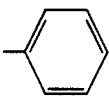
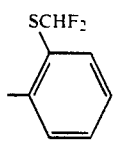 CH₃ 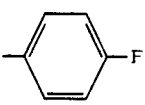
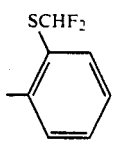 CH₃ 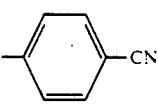
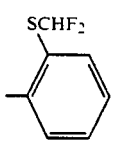 CH₃ 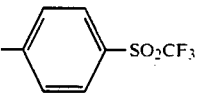
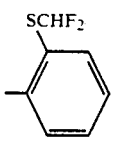 CH₃ 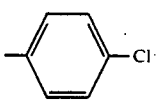
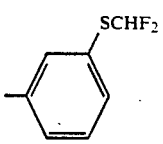 CH₃ 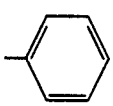
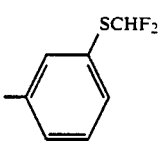 CH₃ 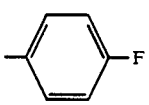
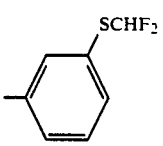 CH₃ 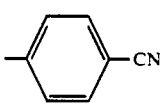

-continued
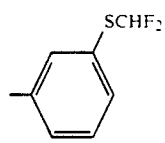 CH₃ 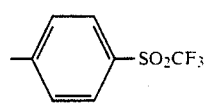
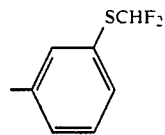 CH₃ 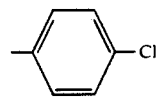
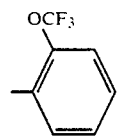 CH₃ 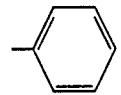
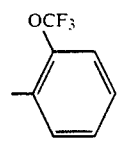 CH₃ 
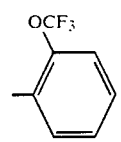 CH₃ 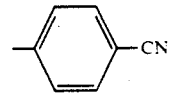
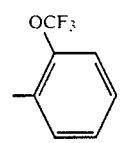 CH₃ 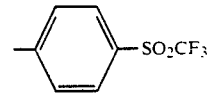
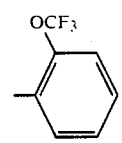 CH₃ 
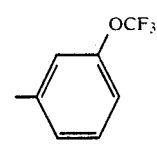 CH₃ 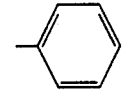
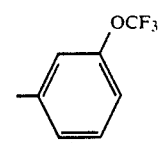 CH₃ 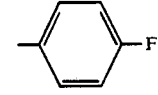
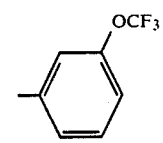 CH₃ 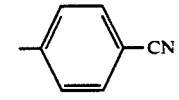
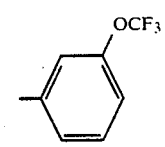 CH₃ 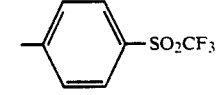

-continued
| | | |
|---|---|---|
| 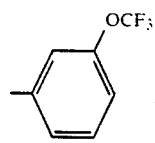 | CH₃ | 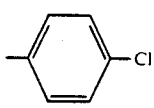 |
| 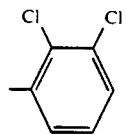 | CH₃ | 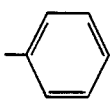 |
| 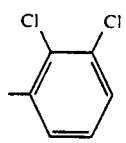 | CH₃ | 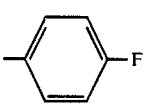 |
| 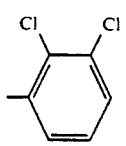 | CH₃ | 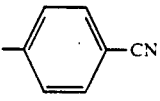 |
| 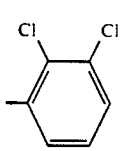 | CH₃ | 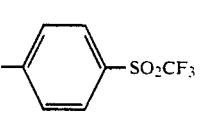 |
| 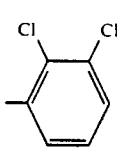 | CH₃ | 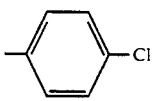 |
| 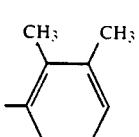 | CH₃ | 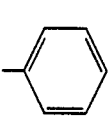 |
| 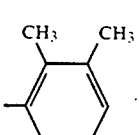 | CH₃ | 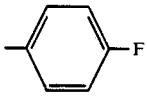 |
| 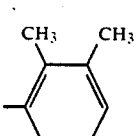 | CH₃ | 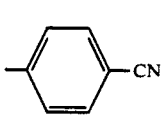 |
| 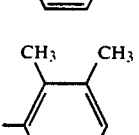 | CH₃ | 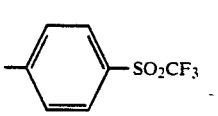 |
| 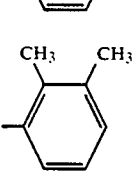 | CH₃ | 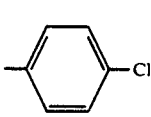 |

-continued
| | | |
|---|---|---|
| 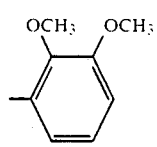 | CH₃ | 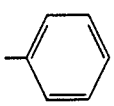 |
| 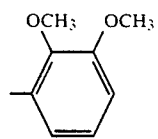 | CH₃ | 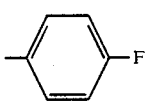 |
| 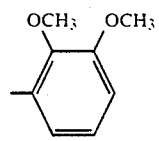 | CH₃ | 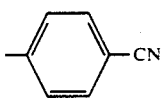 |
| 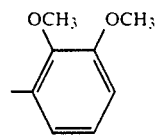 | CH₃ | 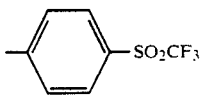 |
| 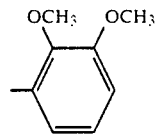 | CH₃ | 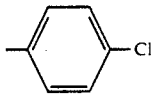 |
| 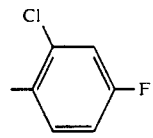 | CH₃ | 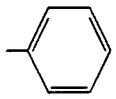 |
| 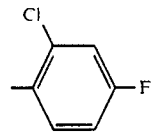 | CH₃ | 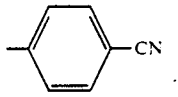 |
| 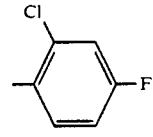 | CH₃ | 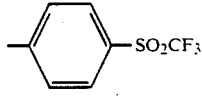 |
| 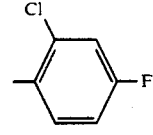 | CH₃ | 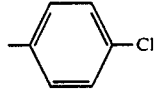 |
| 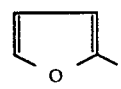 | CH₃ | 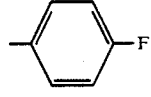 |
| 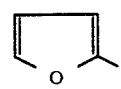 | CH₃ | 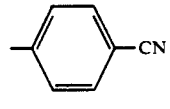 |
| 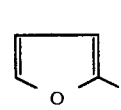 | CH₃ | 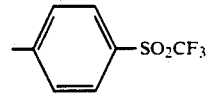 |

-continued
| | | |
|---|---|---|
| 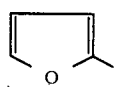 | CH₃ | 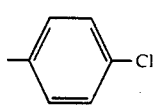—Cl |
| 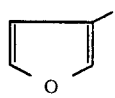 | CH₃ | 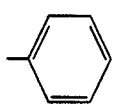 |
| 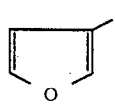 | CH₃ | 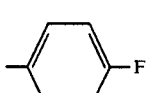—F |
|  | CH₃ | 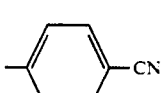—CN |
| 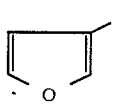 | CH₃ | 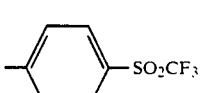—SO₂CF₃ |
| 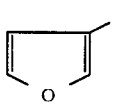 | CH₃ | 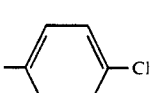—Cl |
| 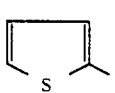 | CH₃ | 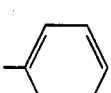 |
| 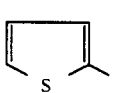 | CH₃ | 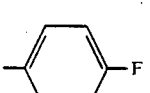—F |
| 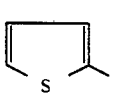 | CH₃ | 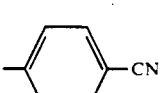—CN |
| 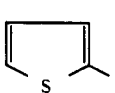 | CH₃ | 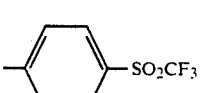—SO₂CF₃ |
| 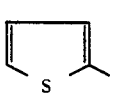 | CH₃ | 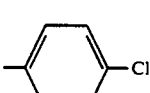—Cl |
|  | CH₃ | 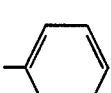 |
|  | CH₃ | 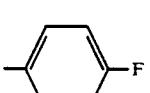—F |
|  | CH₃ | 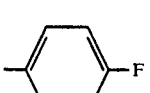—F |

-continued
| | | | |
|---|---|---|---|
| 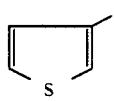 | CH₃ | 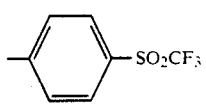 | |
| 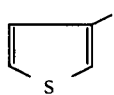 | CH₃ | 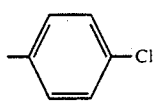 | |
| 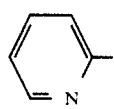 | CH₃ | 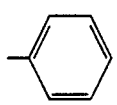 | |
| 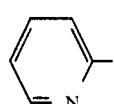 | CH₃ | 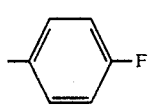 | |
| 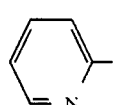 | CH₃ | 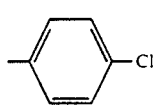 | |
| 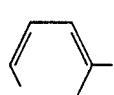 | CH₃ | 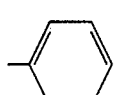 | |
| 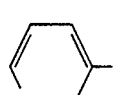 | CH₃ | 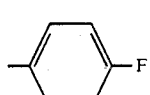 | |
| 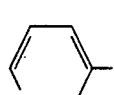 | CH₃ | 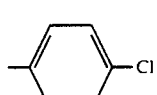 | |
| 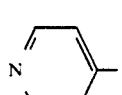 | CH₃ | 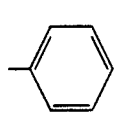 | |
| 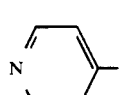 | CH₃ | 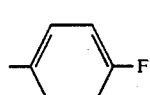 | |
| 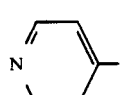 | CH₃ | 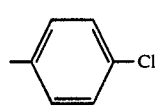 | |
| 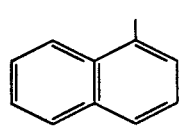 | CH₃ | 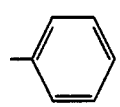 | |
| 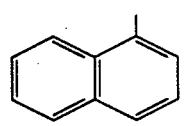 | CH₃ | 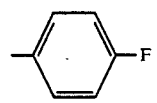 | |

-continued
| | | |
|---|---|---|
| 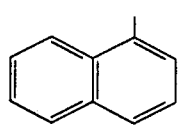 | CH$_3$ | 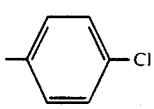 |
| 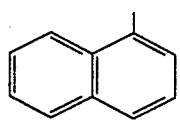 | CH$_3$ | 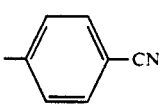 |
| 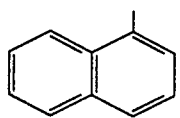 | CH$_3$ | 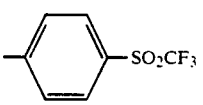 |
| 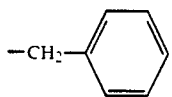 | CH$_3$ | 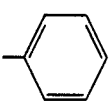 |
| 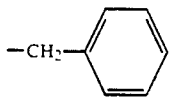 | CH$_3$ | 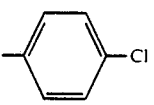 |
| 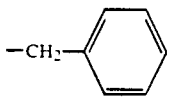 | CH$_3$ | 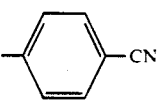 |
| 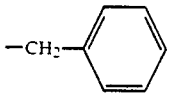 | CH$_3$ | 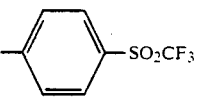 |
| 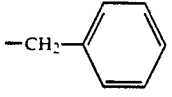 | CH$_3$ | 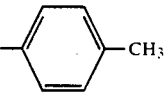 |
| 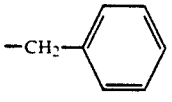 | CH$_3$ | 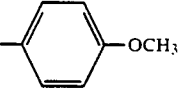 |
| 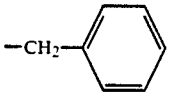 | CH$_3$ | 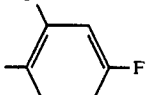 |
| 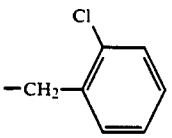 | CH$_3$ | 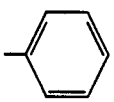 |
| 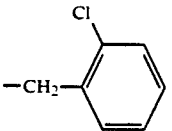 | CH$_3$ | 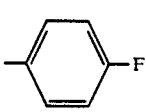 |

-continued
| | | |
|---|---|---|
| 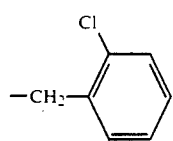 | CH₃ | 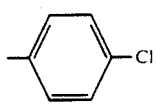 |
| 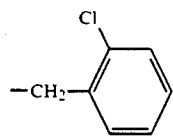 | CH₃ | 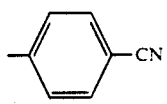 |
| 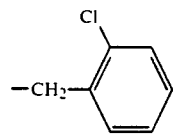 | CH₃ | 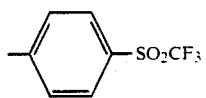 |
| 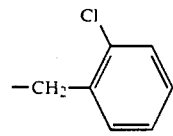 | CH₃ | 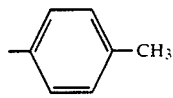 |
| 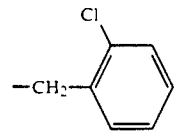 | CH₃ | 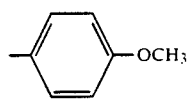 |
| 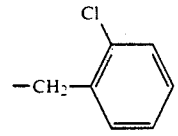 | CH₃ | 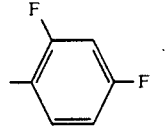 |
| 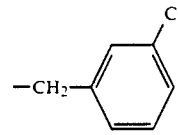 | CH₃ | 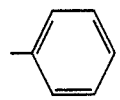 |
| 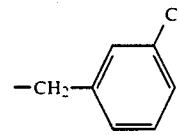 | CH₃ | 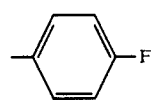 |
| 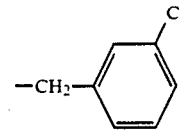 | CH₃ | 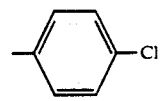 |
| 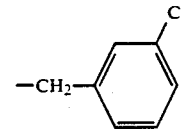 | CH₃ | 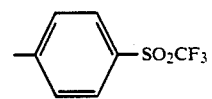 |
| 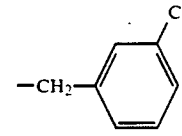 | CH₃ | 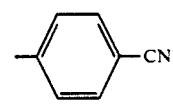 |

-continued
| | | |
|---|---|---|
| 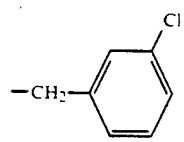 | CH₃ | 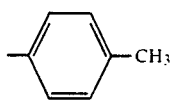—CH₃ |
| 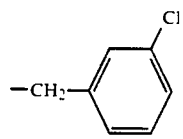 | CH₃ | 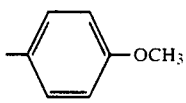—OCH₃ |
| 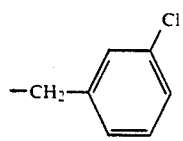 | CH₃ | 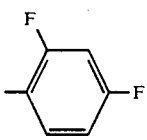 |
| 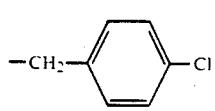 | CH₃ | 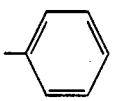 |
| 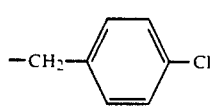 | CH₃ | 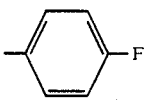 |
| 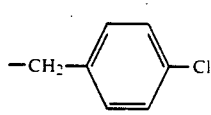 | CH₃ | 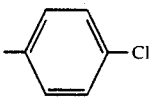 |
| 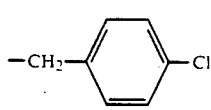 | CH₃ | 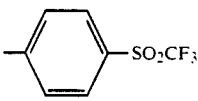 |
| 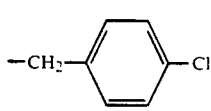 | CH₃ | 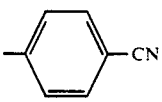 |
| 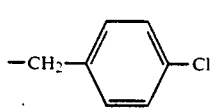 | CH₃ | 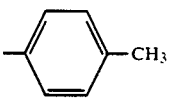 |
| 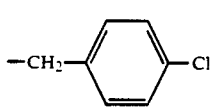 | CH₃ | 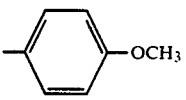 |
| 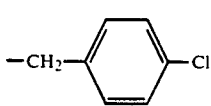 | CH₃ | 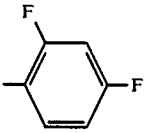 |
| 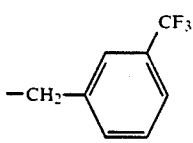 | CH₃ | 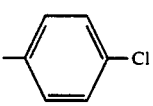 |

| | | | |
|---|---|---|---|
| 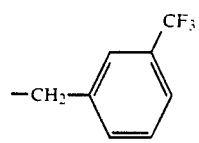 | CH₃ | 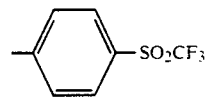 | |
| 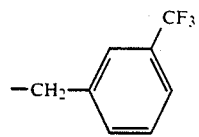 | CH₃ | 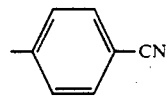 | |
| 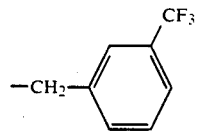 | CH₃ | 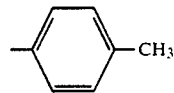 | |
| 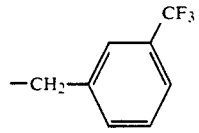 | CH₃ | 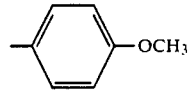 | |
| 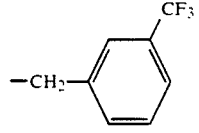 | CH₃ | 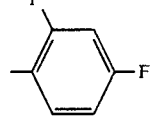 | |
| 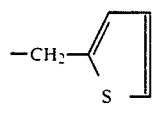 | CH₃ | 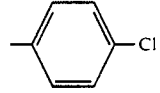 | |
| 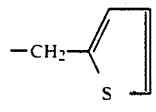 | CH₃ | 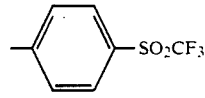 | |
| 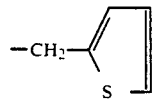 | CH₃ | 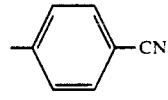 | |
| 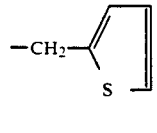 | CH₃ | 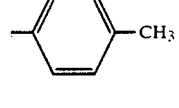 | |
| 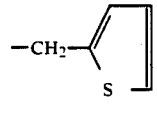 | CH₃ | 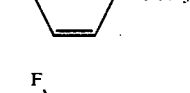 | |
| 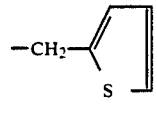 | CH₃ | 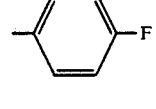 | |
| 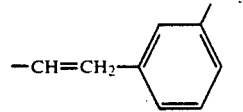 | CH₃ | 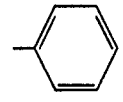 | |

| | |
|---|---|
| 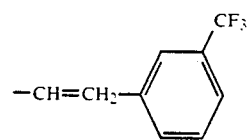 | 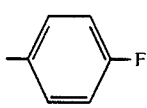 |
| 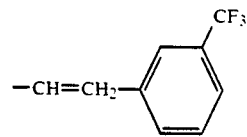 | 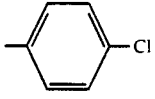 |
| 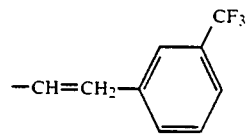 | 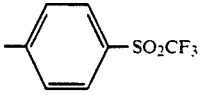 |
| 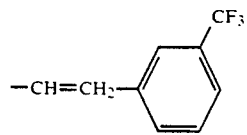 | 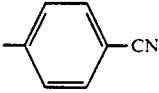 |
| 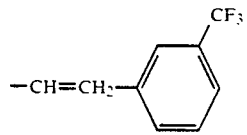 | 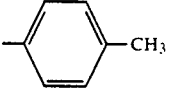 |
| 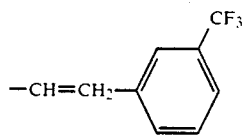 | 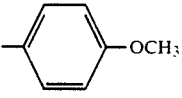 |
| 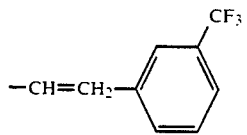 | 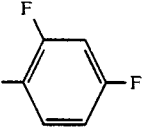 |
| 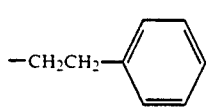 | 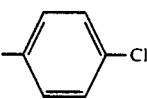 |
| 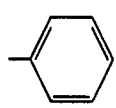 | 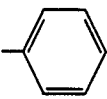 |
| 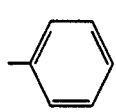 | 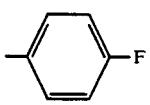 |
| 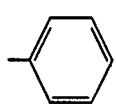 | 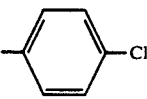 |
| 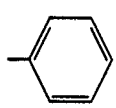 | 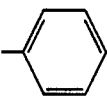 |

-continued
| | | |
|---|---|---|
| 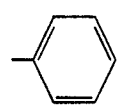 | —CH$_2$CF$_3$ | 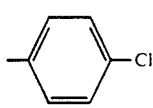 |
| 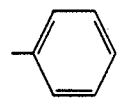 | —CH(CH$_3$)$_2$ | 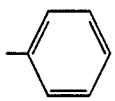 |
| 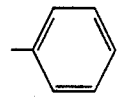 | —CH(CH$_3$)$_2$ | 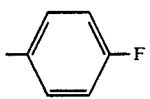 |
| 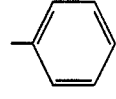 | —CH(CH$_3$)$_2$ | 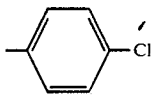 |
| 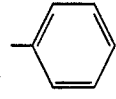 | —C$_3$H$_7$-n | 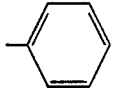 |
| 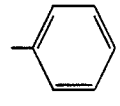 | —C$_3$H$_7$-n | 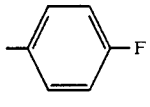 |
| 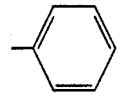 | —C$_3$H$_7$-n | 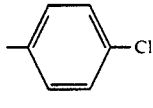 |
| 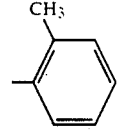 | —CH$_2$CH$_3$ | 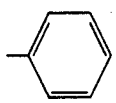 |
| 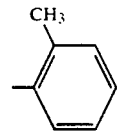 | —CH$_2$CH$_3$ | 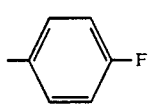 |
| 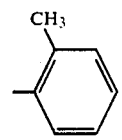 | —CH$_2$CH$_3$ | 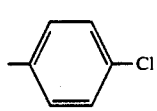 |
| 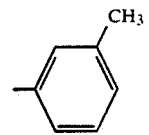 | —CH$_2$CH$_3$ | 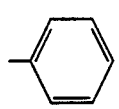 |
| 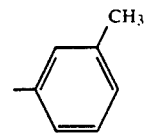 | —CH$_2$CH$_3$ | 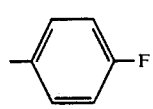 |

-continued
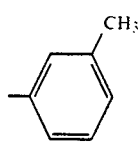 —CH₂CH₃ 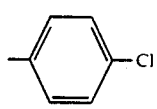
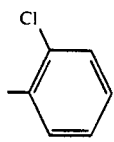 —CH₂CH₃ 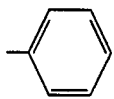
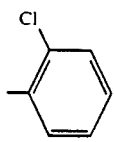 —CH₂CH₃ 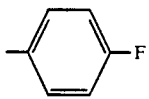
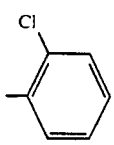 —CH₂CH₃ 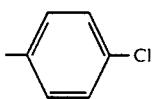
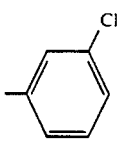 —CH₂CH₃ 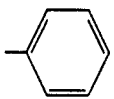
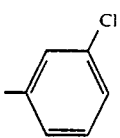 —CH₂CH₃ 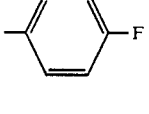
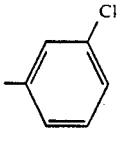 —CH₂CH₃ 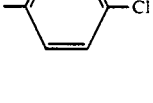
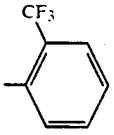 —CH₂CH₃ 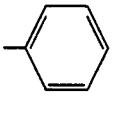
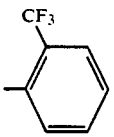 —CH₂CH₃ 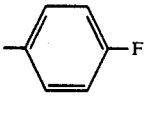
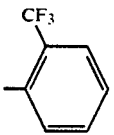 —CH₂CH₃ 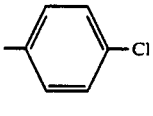
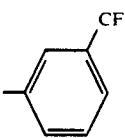 —CH₂CH₃ 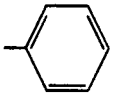

-continued
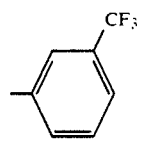 —CH₂CH₃ 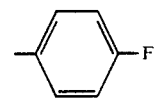
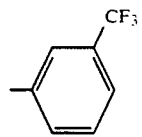 —CH₂CH₃ 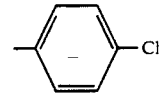
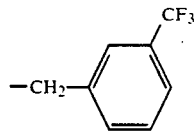 —CH₂CH₃ 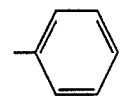
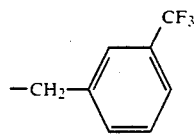 —CH₂CH₃ 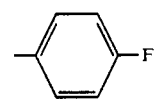
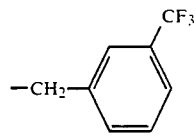 —CH₂CH₃ 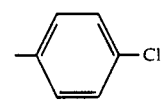
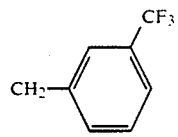 —CH₂CH₃ 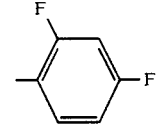
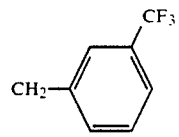 —CH(CH₃)₂ 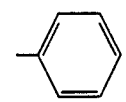
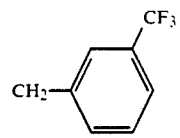 —CH(CH₃)₂ 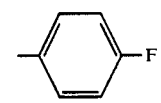
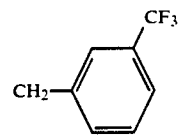 —CH(CH₃)₂ 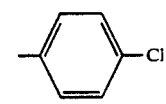
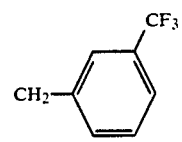 —CH(CH₃)₂ 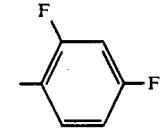
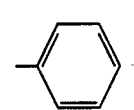 —CH₂—CH=CH₂ 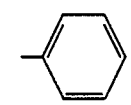

-continued

| | | |
|---|---|---|
| 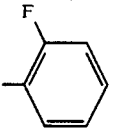 (phenyl) | −CH₂−CH=CH₂ | 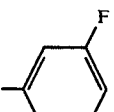 (4-F phenyl) |
| phenyl | −CH₂−CH=CH₂ | 2-Cl,4-F phenyl |
| phenyl | −CH₂−C≡CH | phenyl |
| phenyl | −CH₂−C≡CH | 4-F phenyl |
| phenyl | −CH₂−C≡CH | 4-Cl phenyl |

If, for example, 1-(4-fluorophenyl)-3-phenyl-4-(N,N-dimethylaminomethylidene)-2-pyrazolin-5-one and N-methylhydroxylamine hydrochloride are used as starting materials, the course of the reaction of the process according to the invention can be represented by the following equation:

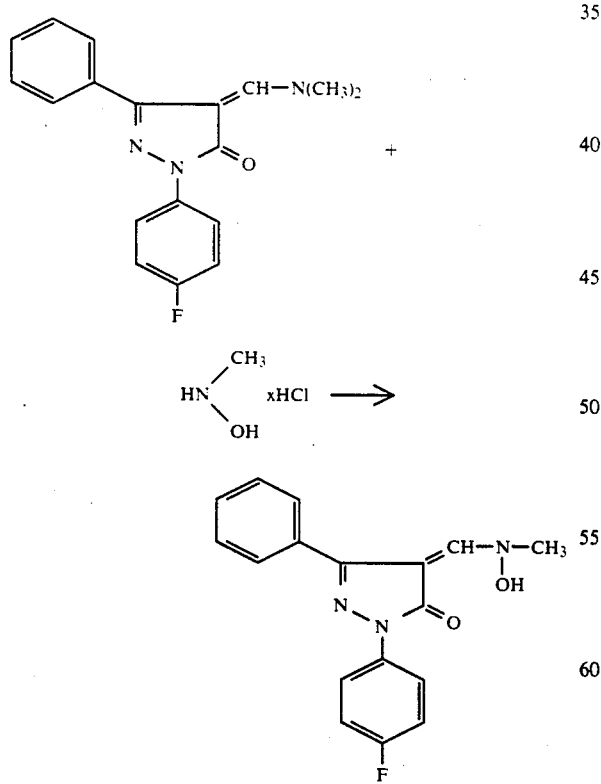

In formula (II), R¹ and Ar preferably or in particular have those meanings which have already been indicated above as preferred or as particularly preferred for R¹ and Ar in connection with the description of the compounds of the formula (I) according to the invention.

Examples of the starting materials of the formula (II) are shown in Table 2.

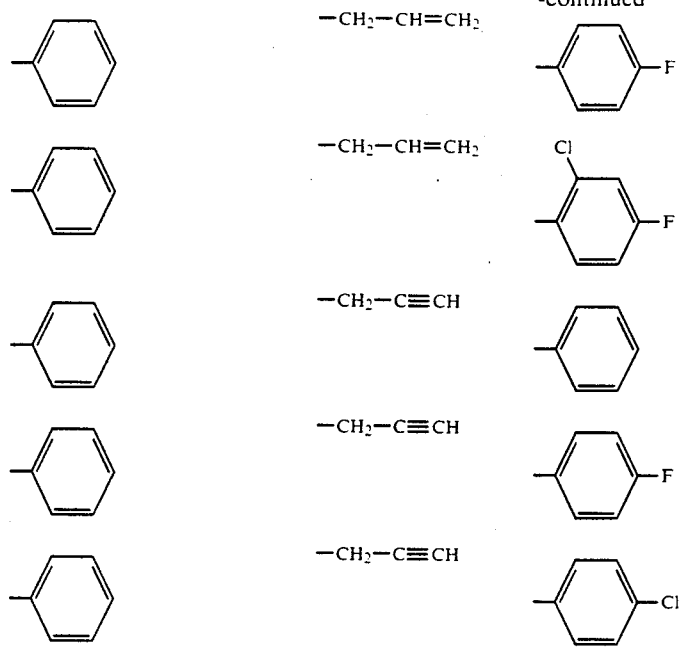

TABLE 2

| R¹ | Ar |
|---|---|
| −C₃H₇-n | 2-F phenyl |
| −C₃H₇-n | 3-F phenyl |
| −C₃H₇-n | 4-Br phenyl |
| −C₃H₇-n | 4-SCF₃ phenyl |
| −C₃H₇-n | 4-CN phenyl |

-continued
| | | |
|---|---|---|
| —C₃H₇-n | 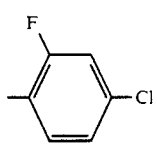 | 5 |
| —CH₂OCH₃ | 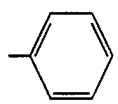 | 10 |
| —CH₂OCH₃ | 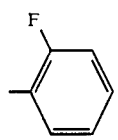 | 15 |
| —CH₂OCH₃ | 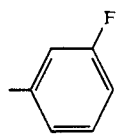 | 20 |
| —CH₂OCH₃ | 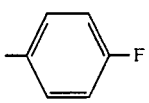 | 30 |
| —CH₂OCH₃ | 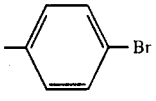 | 35 |
| —CH₂OCH₃ | 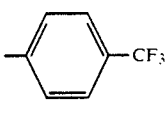 | 40 |
| —CH₂OCH₃ | 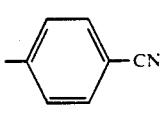 | 45 |
| —CH₂OCH₃ | 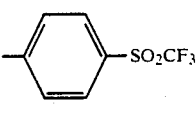 | 50 |
| —CH₂OCH₃ | 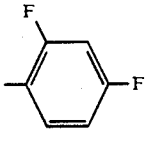 | 55 |
| —C₄H₉-n | 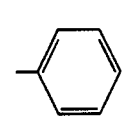 | 60 |
| —C₄H₉-n |  | 65 |
-continued
| | |
|---|---|
| —C₄H₉-n | 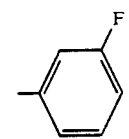 |
| —C₄H₉-n | 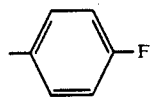 |
| —C₄H₉-n |  |
| —C₄H₉-n | 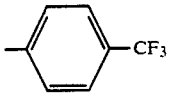 |
| —C₄H₉-n | 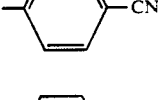 |
| —C₄H₉-n | 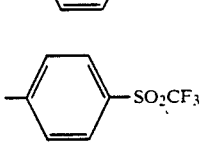 |
| —C₄H₉-n | 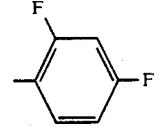 |
| —C₄H₉-n | 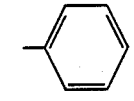 |
| —CH₂—CH(CH₃)₂ | 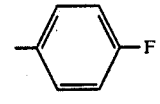 |
| —CH₂—CH(CH₃)₂ | 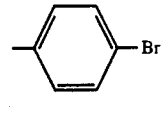 |
| —CH₂—CH(CH₃)₂ | 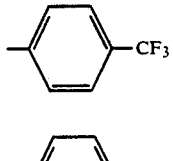 |
| —CH₂—CH(CH₃)₂ | 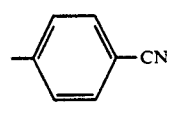 |
| —CH₂—CH(CH₃)₂ | |

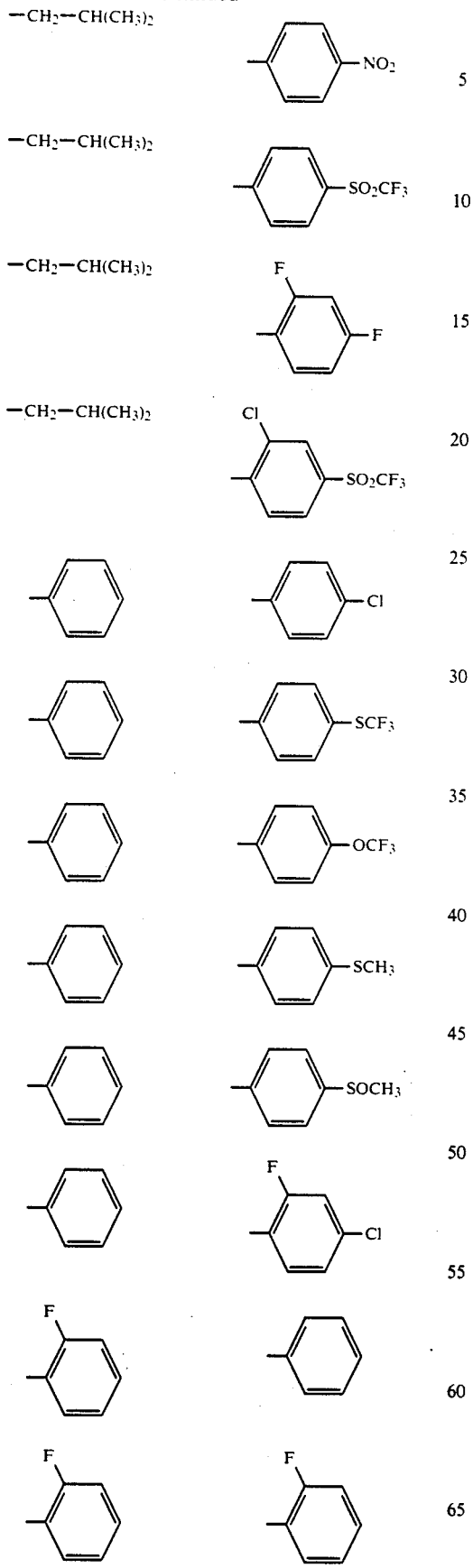
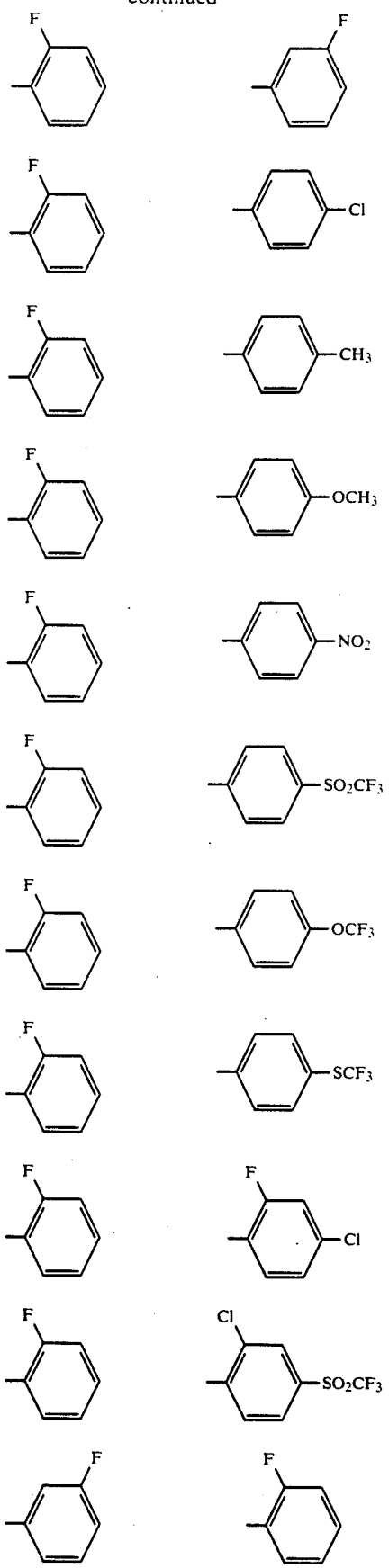

-continued
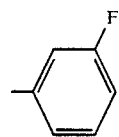 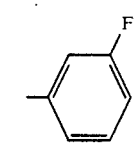
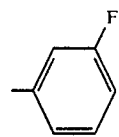 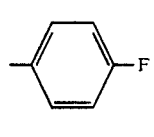
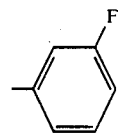 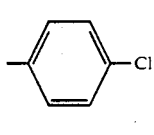
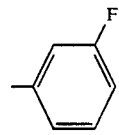 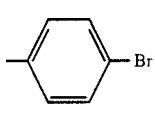
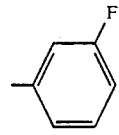 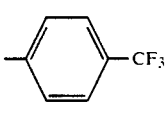
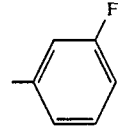 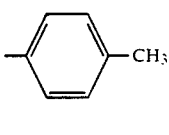
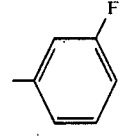 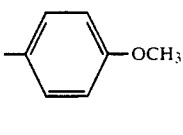
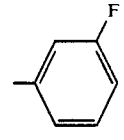 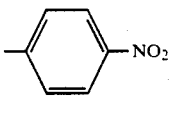
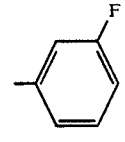 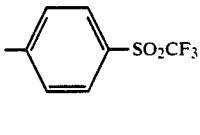
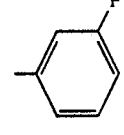 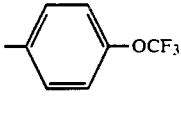
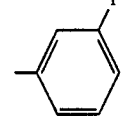 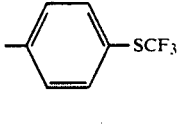
-continued
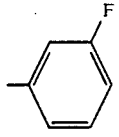 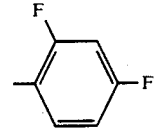
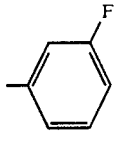 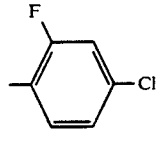
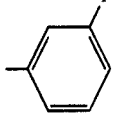 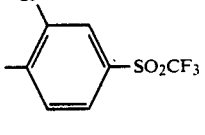
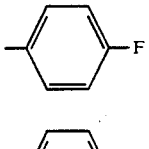 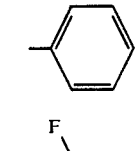
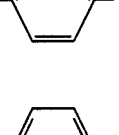 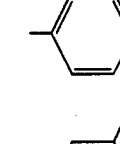
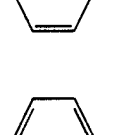 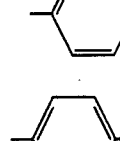
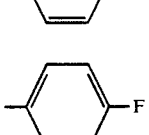 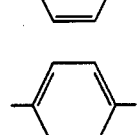
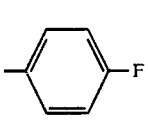 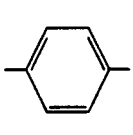
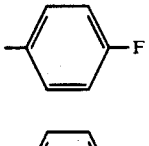 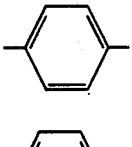
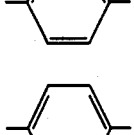 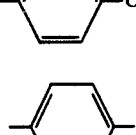
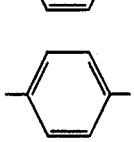 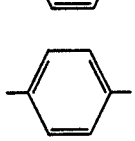

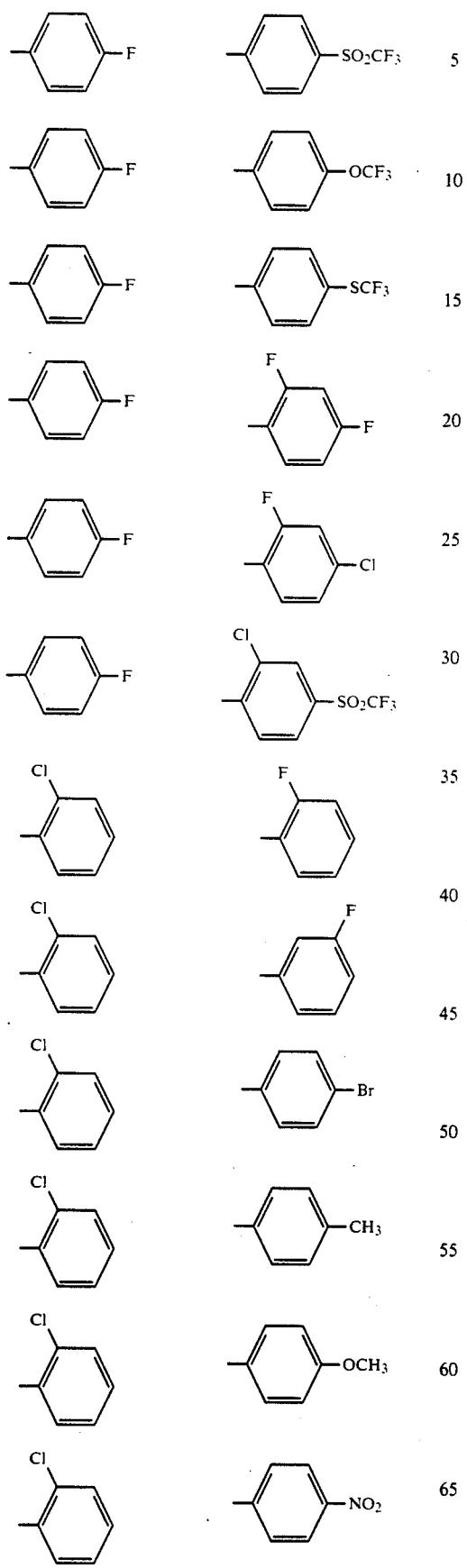
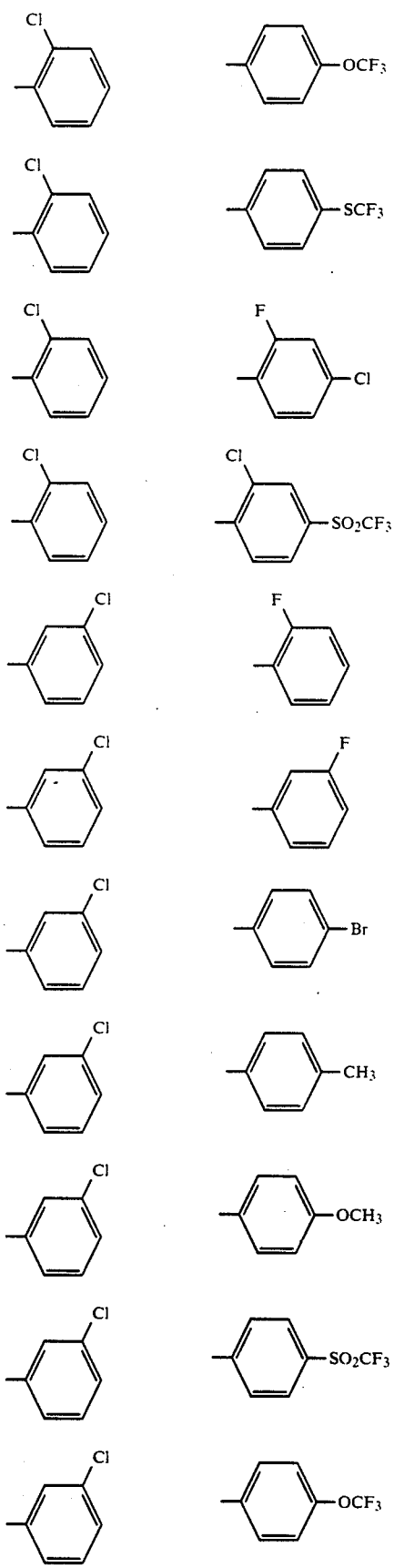

-continued

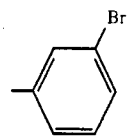 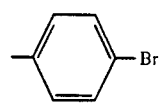 5
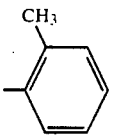 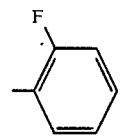
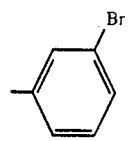 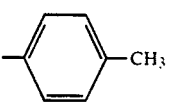 10
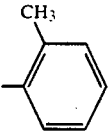 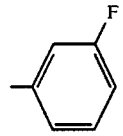
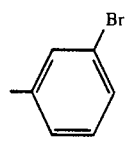 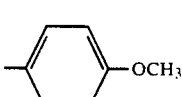 15
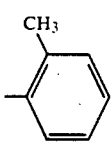 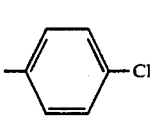
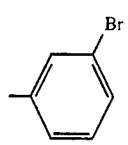 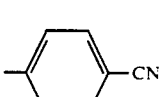 20
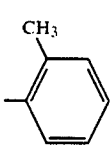 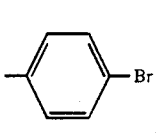
25
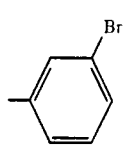 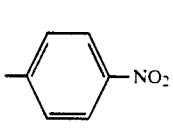 30
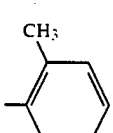 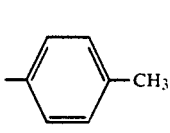
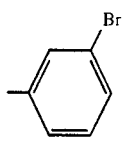 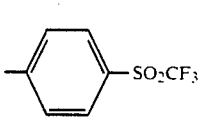 35
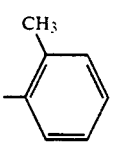 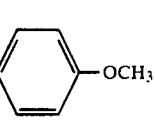
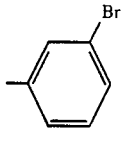 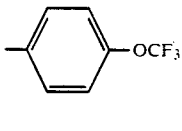 40
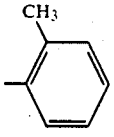 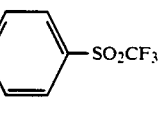
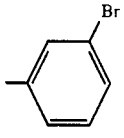 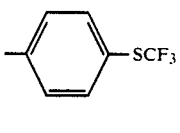 45
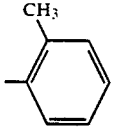 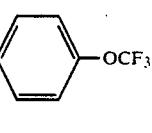
50
55
60
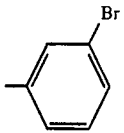 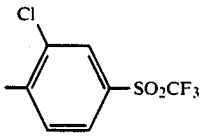 65
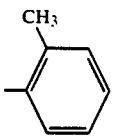 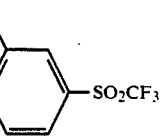

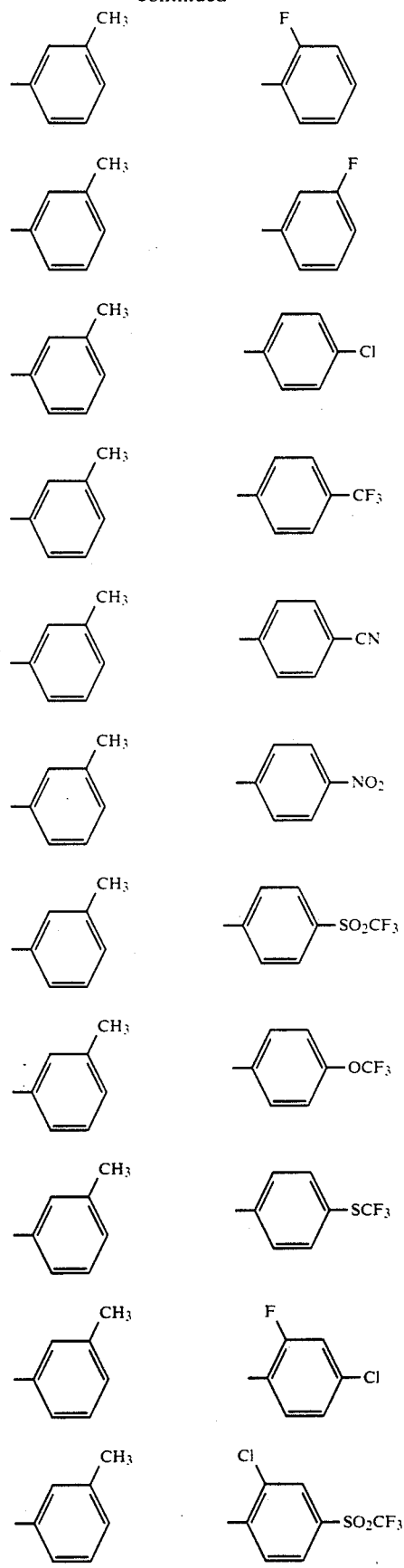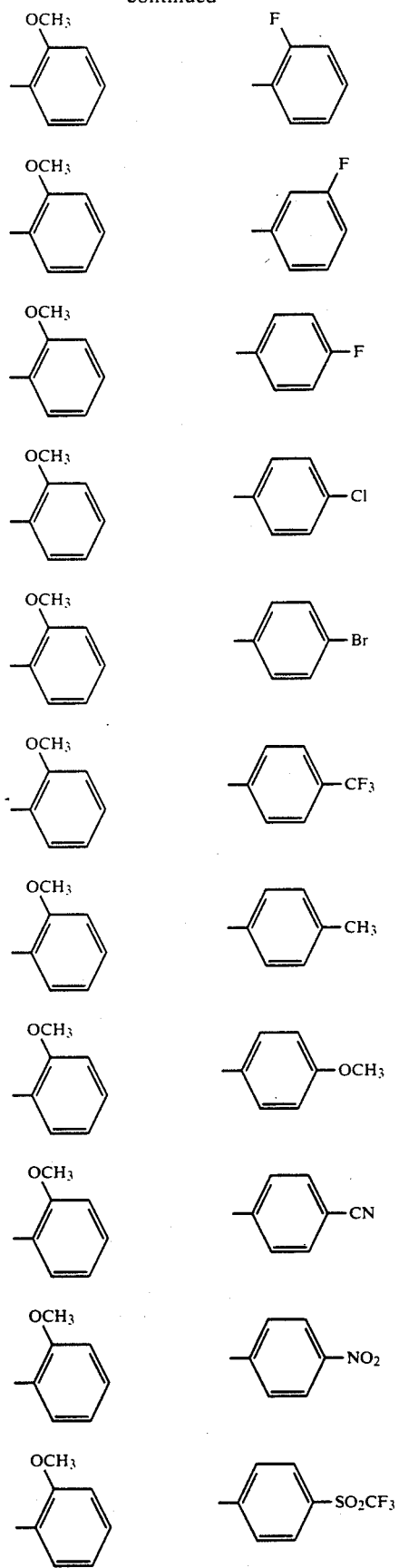

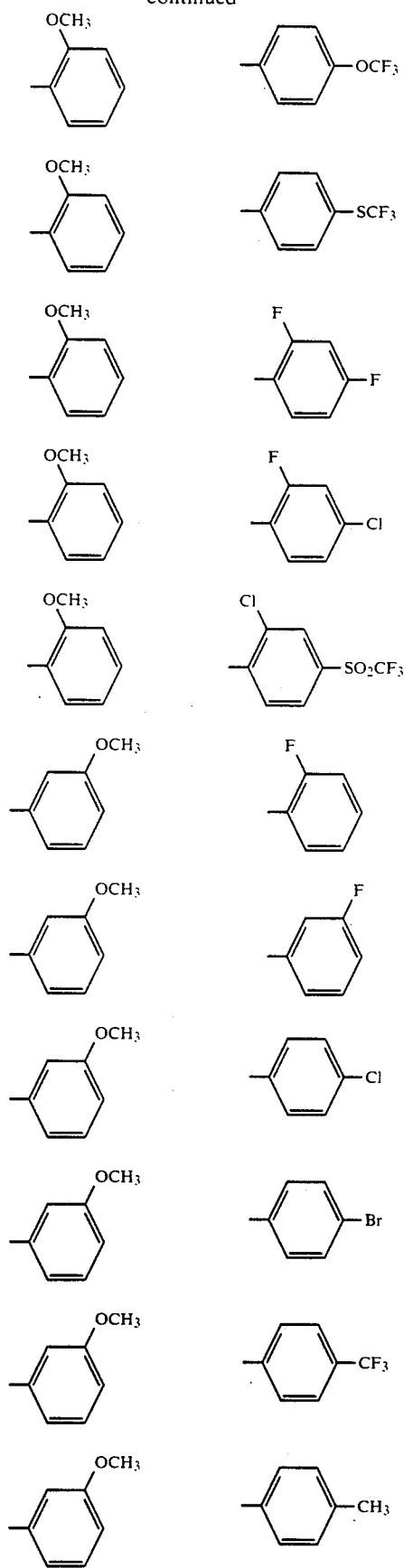
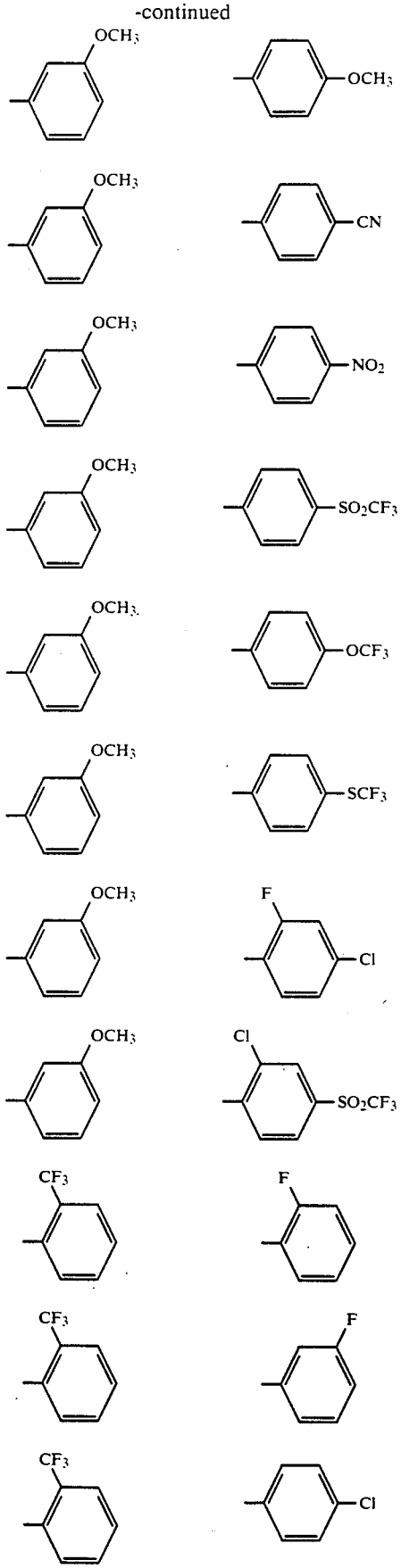

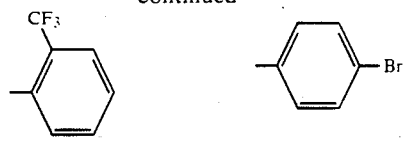 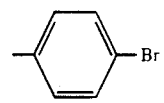
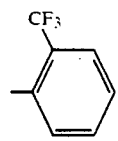 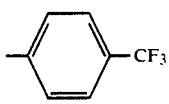
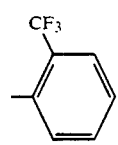 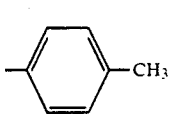
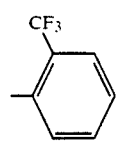 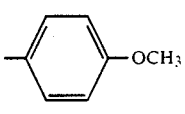
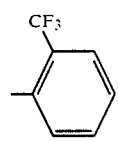 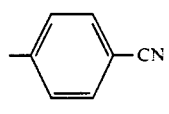
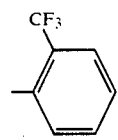 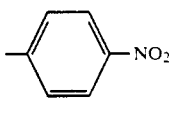
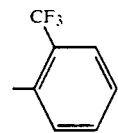 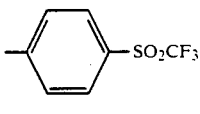
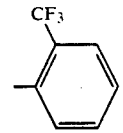 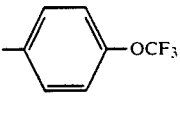
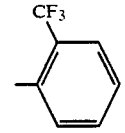 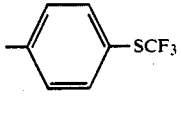
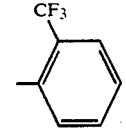 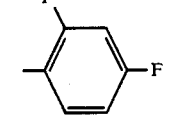
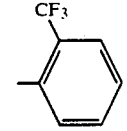 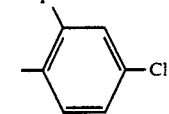
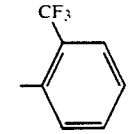 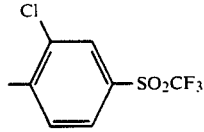
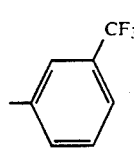 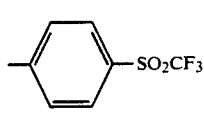
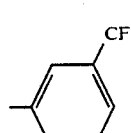 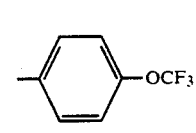
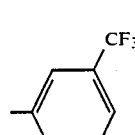 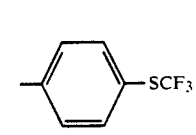
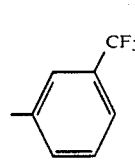 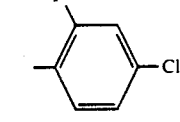
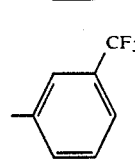 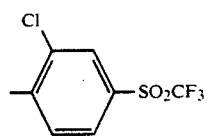
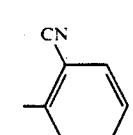 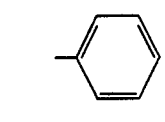
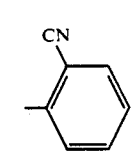 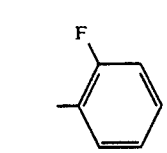
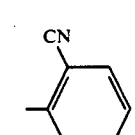 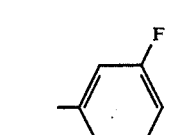
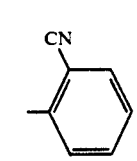 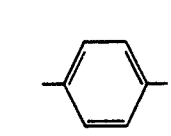
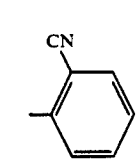 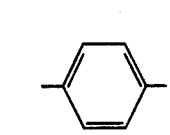

-continued
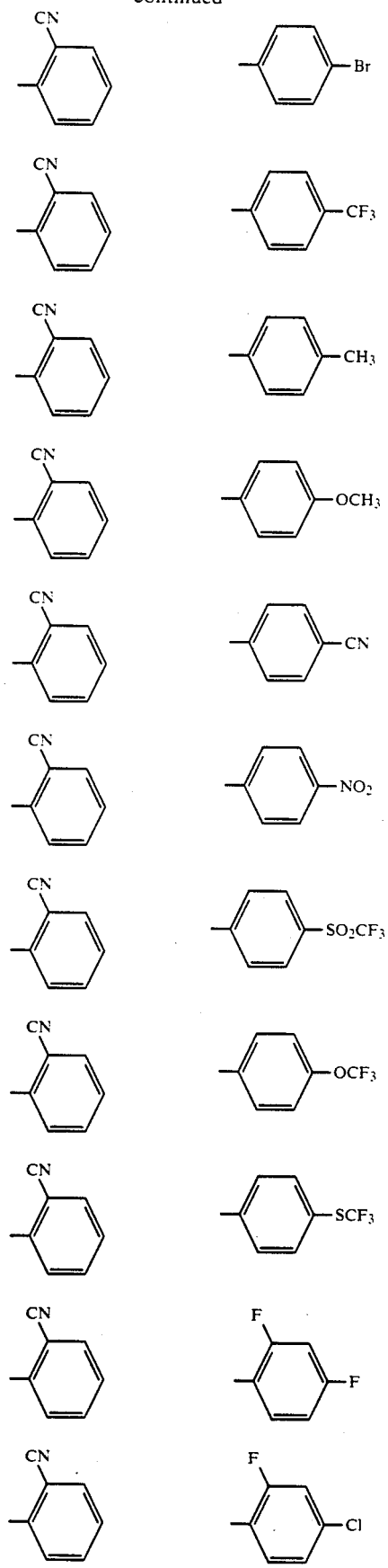
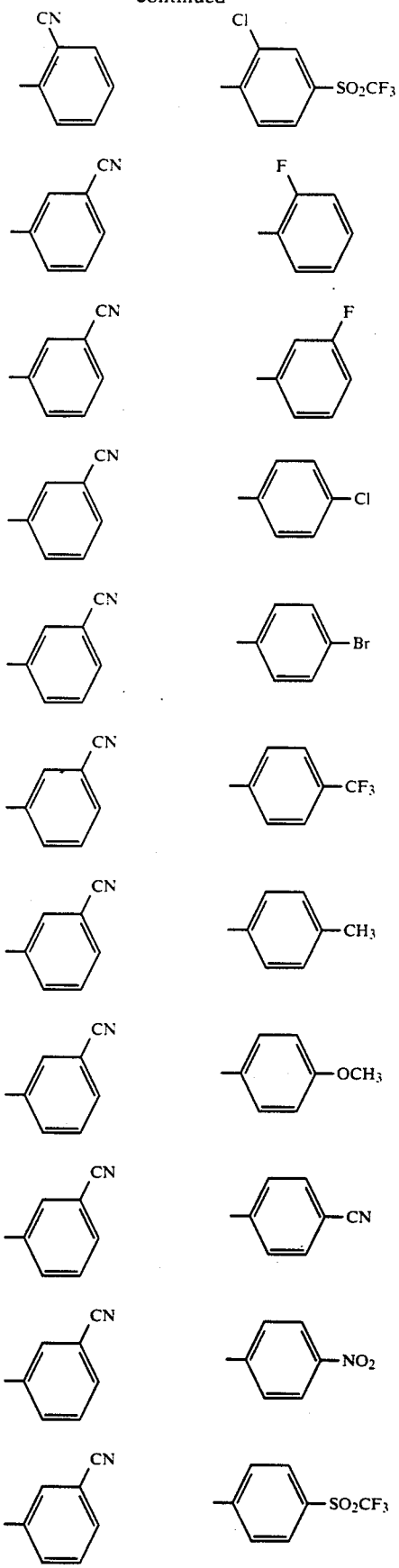

-continued

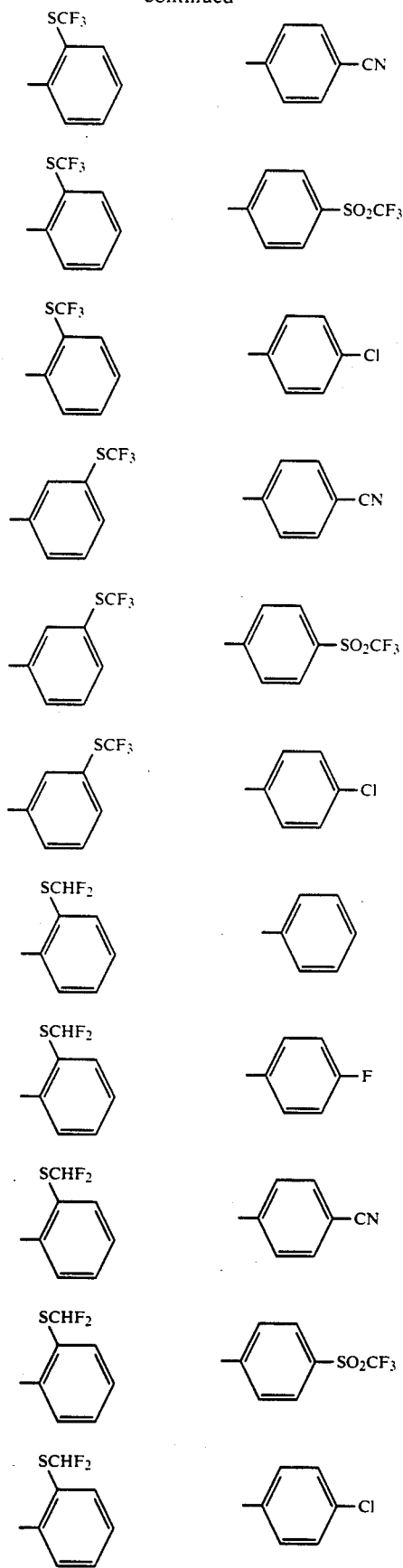
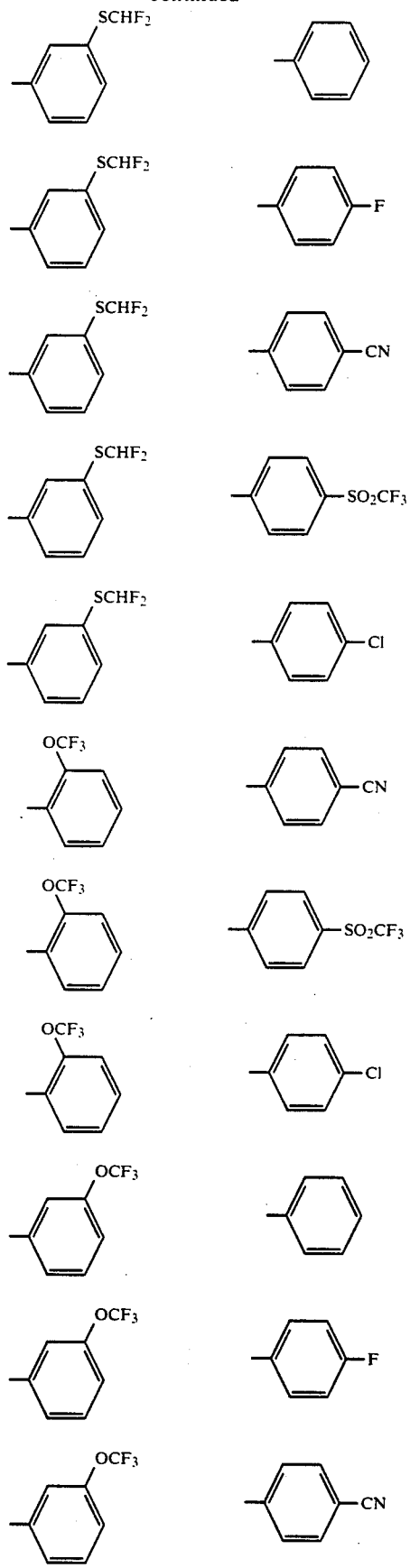

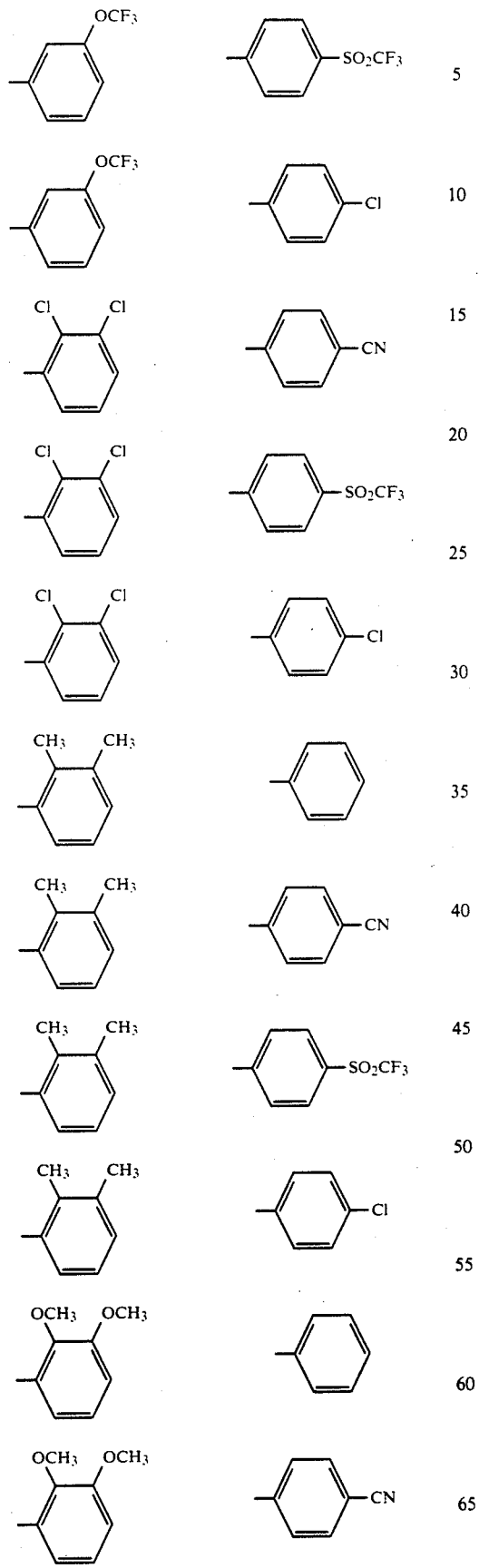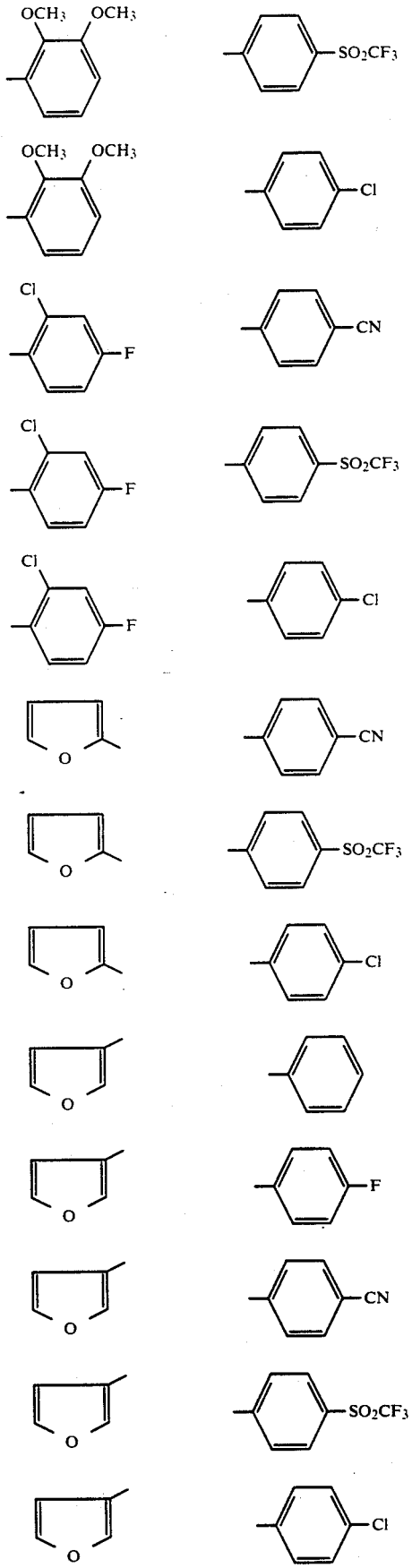

119
-continued
| | | |
|---|---|---|
| 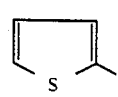 | 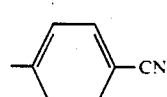 | 5 |
| 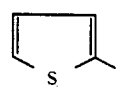 | 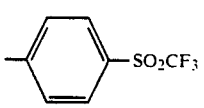 | 10 |
| 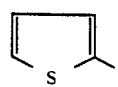 | 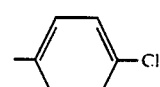 | 15 |
|  | 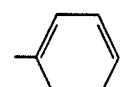 | 20 |
| 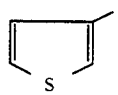 | 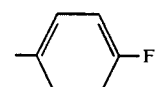 | 25 |
| 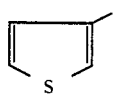 | 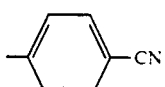 | 30 |
| 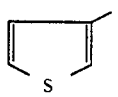 | 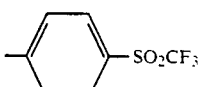 | 35 |
| 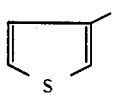 | 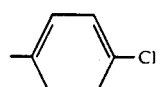 | 40 |
| 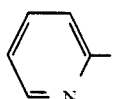 | 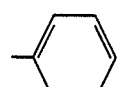 | 45 |
| 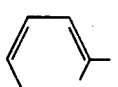 | 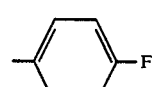 | 50 |
| 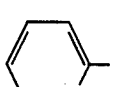 | 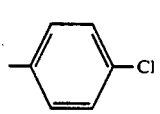 | 55 |
| 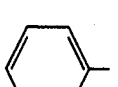 | 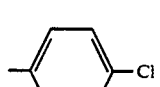 | 60 |
| 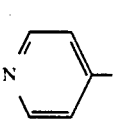 | 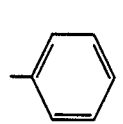 | 65 |
120
-continued
| | |
|---|---|
| 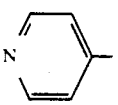 | 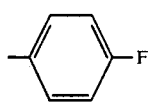 |
| | 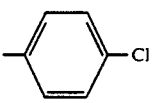 |
| | 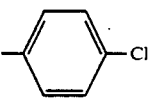 |
| | 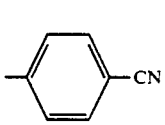 |
| | 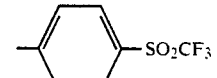 |
| 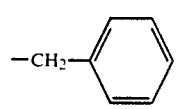 | 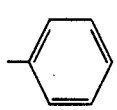 |
| 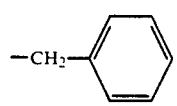 | 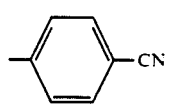 |
| 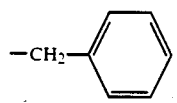 | 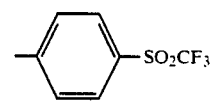 |
| 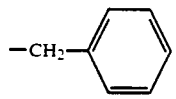 | 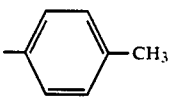 |
| 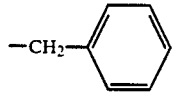 | 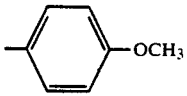 |
| 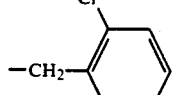 | 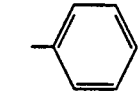 |
| 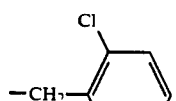 | 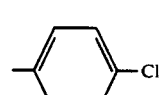 |

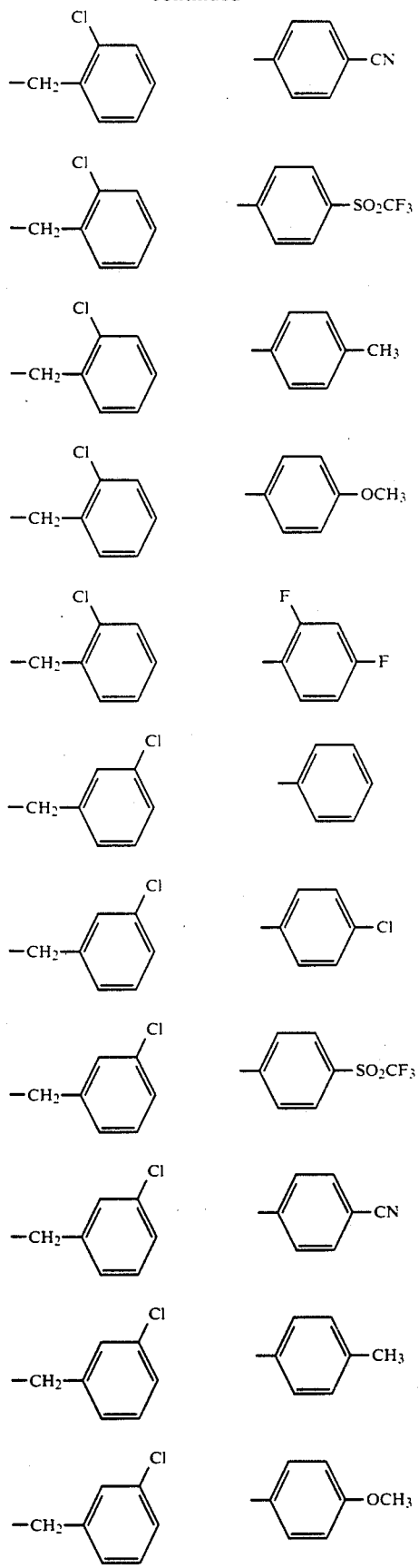
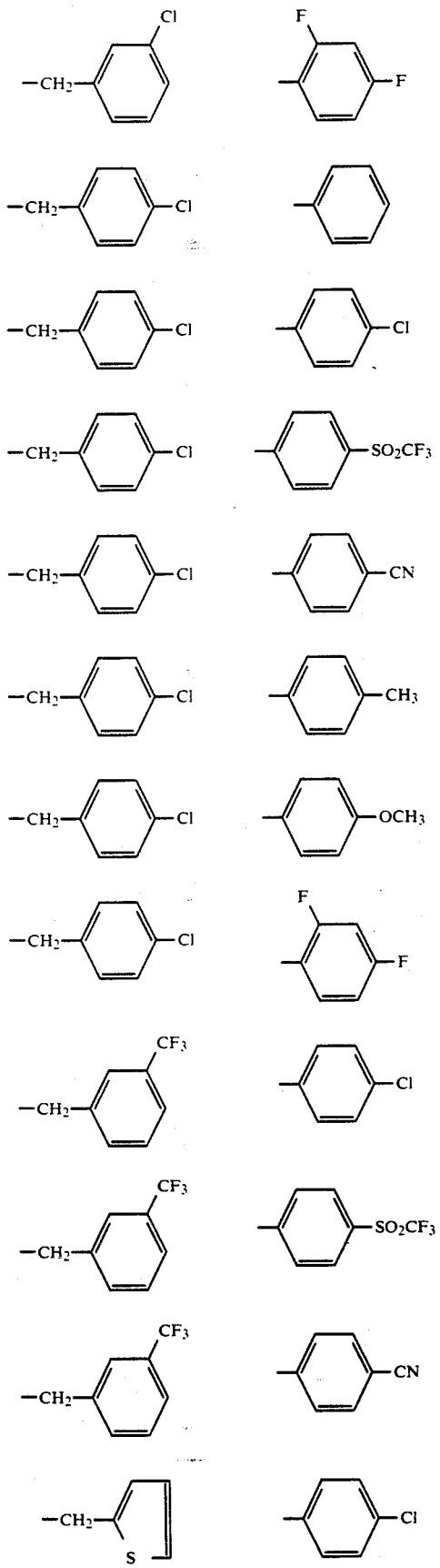

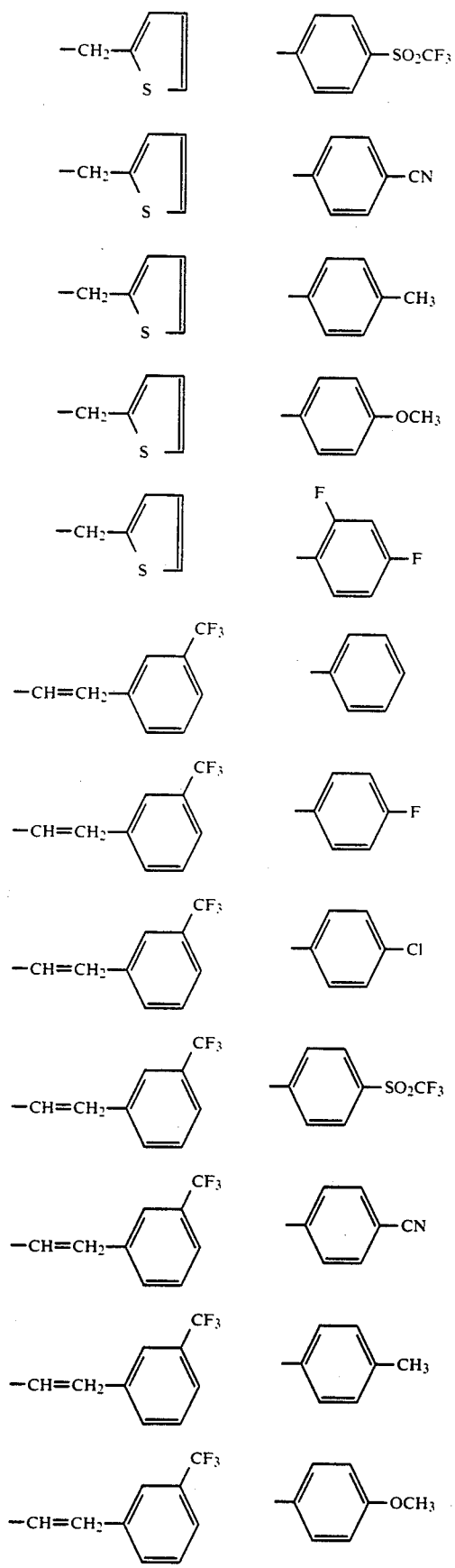
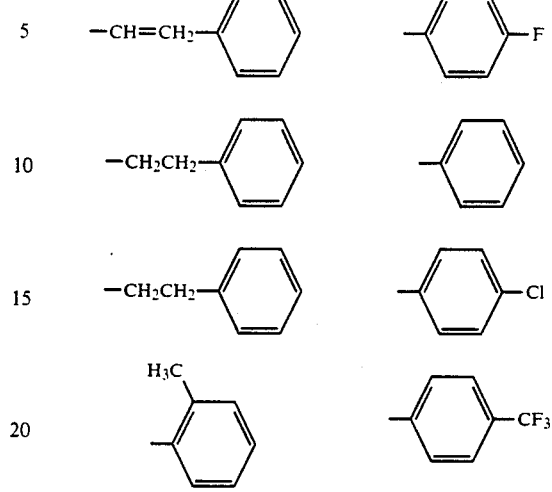

The dimethylaminomethylidene-pyrazolin-5-one derivatives of the formula (II) are known and/or can be prepared by known processes (compared EP 0,274,642).

In formula (III), $R^2$ preferably or in particular has those meanings which have already been indicated above as preferred or as particularly preferred for $R^2$ in connection with the description of the compounds of the formula (I) according to the invention and HX represents an equivalent of a mineral acid such as, for example, hydrochloric acid or a carboxylic acid such as, for example, oxalic acid, preferably hydrochloric acid.

The hydroxylamine hydrochloride derivatives of the formula (III) are generally known compounds of organic chemistry.

The process according to the invention for the preparation of the new pyrazolin-5-one-derivatives of the formula (I) is preferably carried out using diluents. Suitable diluents here are virtually all inert organic solvents. These preferably include aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as, for example, acetonitrile and propionitrile, amides such as, for example, dimethylformamide, dimethylacetamide and N-methyl-pyrrolidone and also dimethyl sulphoxide, tetramethylene sulphone and hexamethylphosphoramide.

The reaction temperatures can be varied within a relatively wide range in the process according to the invention. In general, the process is carried out at temperatures between 0° C. and +100° C., preferably at temperatures between +10° C. and +50° C.

In order to carry out the process according to the invention, 1 to 3 moles, preferably 1 to 1.5 moles of hydroxylamine hydrochloride derivative of the formula (III) are in general employed per mole of dimethylaminomethylidene-pyrazolin-5-one derivative of the formula (II). The reaction products are worked up and isolated by generally customary methods.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention are particularly well suited in this case for the selective combating of weeds in annual cultures in the pre-emergence and post-emergence methods.

When used in the post-emergence method, the active compounds according to the invention can be applied alone or in combination with emulsifiable oils, surface-active substances and other additives.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural minerals such as calcite, marble, pumice, sepiolite and dolomite, as well as synthetic granules of inorganic and organic meals, and granules of organic material such as sawdust, coconut shells, corn cobs and tobacco stalks; as emulsifying and/or foamforming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

For combating weeds, the active compounds according to the invention, as such or in the form of their formulations, can also be used as mixtures with known herbicides, finished formulations or tank mixes being possible.

Suitable herbicides for the mixtures are known herbicides, such as, for example, 1-amino-6-ethylthio-3-(2,2-dimethylpropyl)-1,3,5-triazine-2,4(1H,3H)-dione (AMETHYDIONE) or N-(2-benzothiazolyl)-N,N'-dimethylurea (METABENZTHIAZURON) for combating weeds in cereals; 4-amino-3-methyl-6-phenyl-1,2,4-triazin-5(4H)-one (METAMITRON) for combating weeds in sugar beets and 4-amino-6-(1,1-dimethylethyl)-3-methylthio-1,2,4-triazin-5(4H)-one (METRIBUZIN) for combating weeds in soy beans, furthermore also 2,4-dichlorophenoxyacetic acid (2,4-D); 4-(2,4-dichlorophenoxy)-butyric acid (2,4-DB); 2,4-dichlorophenoxypropionic acid (2,4-DP); 5-(2-chloro-4-trifluoromethyl-phenoxy)-2-nitro-benzoic acid (ACIFLUORFEN); 2-chloro-2',6'-diethyl-N-methoxymethylacetanilide (ALACHLOR); 2-chloro-4-ethylamino-6-isopropylamino-1,3,5-triazine(ATRAZINE);3-isopropyl-2,1,3-benzothiadiazin-4-one 2,2-dioxide (BENTAZONE); methyl 5-(2,4-dichlorophenoxy)-2-nitrobenzoate (BIFENOX); 3,5-dibromo-4-hydroxy-benzonitrile (BROMOXYNIL); ethyl 2-{[(4-chloro-6-methoxy-2-pyrimidinyl)-aminocarbonyl-]aminosulphonyl}-benzoate (CHLORIMURON); 2-chloro-N-{[(4-methoxy-6-methyl-1,3,5-triazin-2-yl)-amino]-carbonyl}-benzenesulphonamide (CHLORSULFURON); N,N-dimethyl-N'-(3-chloro-4-methylphenyl)-urea (CHLORTOLURON); 2-[4-(2,4-dichlorophenoxy)-phenoxy]-propionic aicd, its methyl ester or its ethyl ester (DICLOFOP); 4-amino-6-t-butyl-3-ethylthio-1,2,4-triazin-5(4H)-one(ETHIOZIN);2-{4-[(6-chloro-2-benzoxazolyl)-oxy]-phenoxy}-propanoic acid, its methyl ester or its ethyl ester (FENOXAPROP); [(4-amino-3,5-dichloro-6-fluoro-2-pyridinyl)-oxy]-acetic acid or its 1-methylheptyl ester (FLUROXYPYR); 5-(2-chloro-4-trifluoromethyl-phenoxy)-N-methylsulphonyl-2-nitrobenzamide (FOMESAFEN); methyl 2-[4,5-dihydro-4-methyl-4-(1-methylethyl)-5-oxo-1H-imidazol-2-yl)-4-(5)-methylbenzoate (IMAZAMETHABENZ); 3,5-diiodo-4-hydroxybenzonitrile (IOXYNIL); N,N-dimethyl-N'-(4-isopropylphenyl)urea (ISOPROTURON); (2-methyl-4-chlorophenoxy)-acetic acid (MCPA); ((4-chloro-2-methylphenoxy)-propionic acid (MCPP); N-methyl-2-(1,3-benzothiazol-2-yloxy)-acetanilide (MEFENACET); 2-chloro-N-(2,6-dimethylphenyl)-N-[(1H)-pyrazol-1-ylmethyl]-acetamide (METAZACHLOR); 2-ethyl-6-methyl-N-(1-methyl-2-methoxyethyl)-chloroacetanilide (METOLACHLOR); 2-{[[((4-methoxy-6-methyl-1,3,5-triazin-2-yl)-amino)-carbonyl]-amino]-sulphonyl}-benzoic acid or its methyl ester (METSULFURON); N-(1-ethylpropyl)-3,4-dimethyl-2,6-dinitroaniline(PENDIMETHALIN); O-(6-chloro-3-phenyl-pyridazin-4-yl) S-octyl thiocarbonate (PYRIDATE); 4-ethylamino-2-t-butylamino-6-methylthio-s-triazine (TERBUTRYNE); methyl 3-[[[[4-methoxy-6-methyl-1,3,5-triazin-2-yl)-amino]-carbonyl]-amino]-sulphonyl]-thiophene-2-carboxylate (THIAMETURON); S-(2,3,3-trichloroallyl) diisopropylthiocarbamate (TRIALLATE) and 2,6-dinitro-4-trifluoromethyl-N,N-dipropylaniline (TRIFLURALIN). Surprisingly, some mixtures also show a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.001 and 10 kg of active compound per hectare of soil surface, preferably between 0.01 and 5 kg per ha.

The preparation and use of the active compounds according to the invention can be seen from the following examples.

Preparation Example

Example 1

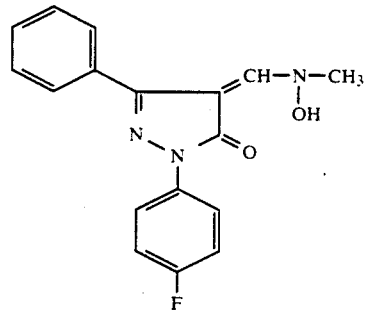

1.54 g (0.005 mol) of 1-(4-fluorophenyl)-3-phenyl-4-(N,N-dimethylaminomethylidene)-2-pyrazolin-5-one are dissolved in 50 ml of methanol, 0.41 g (0.005 mol) of N-methylhydroxylamine hydrochloride is added and the mixture is then stirred at room temperature until conversion is complete (chromatographic checking). The reaction solution is then strongly concentrated, and the solid obtained is taken up with water and filtered off with suction. For purification, the solid is washed several times with water and finally with petroleum ether.

1.3 g (83% of theory) of 1-(4-fluorophenyl)-3-phenyl-4-(N-methyl-N-hydroxyaminomethylidene)-pyrazolin-5-one of melting point 157° C. are obtained.

The pyrazolin-5-one derivatives of the general formula (I)

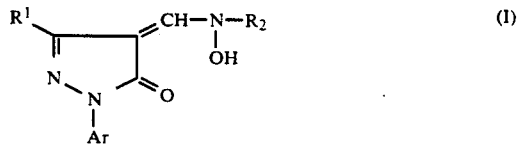

shown in Table 3 are obtained analogously to Preparation Example 1 and according to the general directions for the process according to the invention.

TABLE 3

| Ex. No. | R¹ | R² | Ar | melting point |
|---|---|---|---|---|
| 2 | —C₃H₇-n | CH₃ | 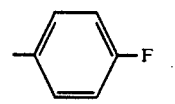 | 149° C. |

TABLE 3-continued
| Ex. No. | R¹ | R² | Ar | melting point |
|---|---|---|---|---|
| 3 | —C₃H₇-n | CH₃ | 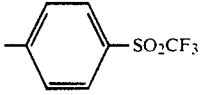 4-SO₂CF₃-C₆H₄ | 143° C. |
| 4 | —CH₂OCH₃ | CH₃ | 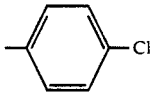 4-Cl-C₆H₄ | 127-128° C. |
| 5 | —CH₂OCH₃ | CH₃ | 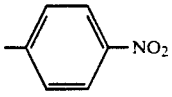 4-NO₂-C₆H₄ | 151° C. |
| 6 | 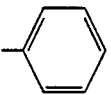 C₆H₅ | CH₃ | 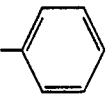 C₆H₅ | 110° C. |
| 7 | 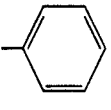 C₆H₅ | CH₃ | 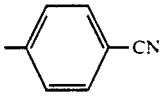 4-CN-C₆H₄ | 185° C. |
| 8 | 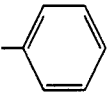 C₆H₅ | CH₃ | 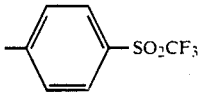 4-SO₂CF₃-C₆H₄ | 214-215° C. |
| 9 | 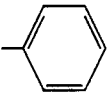 C₆H₅ | CH₃ | 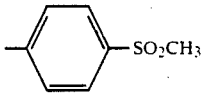 4-SO₂CH₃-C₆H₄ | 185° C. |
| 10 | 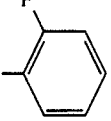 2-F-C₆H₄ | CH₃ | 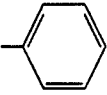 C₆H₅ | 135-136° C. |
| 11 | 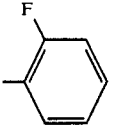 2-F-C₆H₄ | CH₃ | 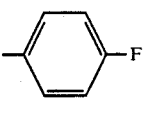 4-F-C₆H₄ | 197-201° C. |
| 12 | 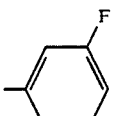 3-F-C₆H₄ | CH₃ | 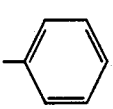 C₆H₅ | 137-138° C. |
| 13 | 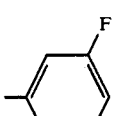 3-F-C₆H₄ | CH₃ | 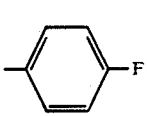 4-F-C₆H₄ | 168-169° C. |
| 14 | 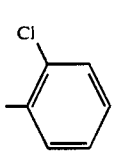 2-Cl-C₆H₄ | CH₃ | 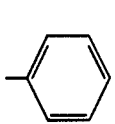 C₆H₅ | 155-156° C. |

TABLE 3-continued

| Ex. No. | R¹ | R² | Ar | melting point |
|---|---|---|---|---|
| 15 | 2-Cl-C₆H₄ | CH₃ | 4-F-C₆H₄ | 145–146° C. |
| 16 | 2-Cl-C₆H₄ | CH₃ | 4-(SO₂CH₃)-C₆H₄ | 197–198° C. |
| 17 | 3-Cl-C₆H₄ | CH₃ | C₆H₅ | 145–146° C. |
| 18 | 3-Cl-C₆H₄ | CH₃ | 4-F-C₆H₄ | 171° C. |
| 19 | 3-Cl-C₆H₄ | CH₃ | 4-CN-C₆H₄ | 100° C. |
| 20 | 3-Cl-C₆H₄ | CH₃ | 4-(SO₂CH₃)-C₆H₄ | 193–194° C. |
| 21 | 3-Br-C₆H₄ | CH₃ | C₆H₅ | 148° C. |
| 22 | 2-CH₃-C₆H₄ | CH₃ | C₆H₅ | 132° C. |
| 23 | 2-CH₃-C₆H₄ | CH₃ | 4-F-C₆H₄ | 86–87° C. |
| 24 | 2-OCH₃-C₆H₄ | CH₃ | C₆H₅ | 124–125° C. |
| 25 | 2-OCH₃-C₆H₄ | CH₃ | 4-F-C₆H₄ | 130–131° C. |

TABLE 3-continued
| Ex. No. | R¹ | R² | Ar | melting point |
|---|---|---|---|---|
| 26 | 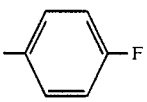 3-OCH₃-C₆H₄ | CH₃ |  4-F-C₆H₄ | 161–162° C. |
| 27 | 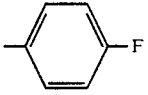 3-CF₃-C₆H₄ | CH₃ | C₆H₅ | 189–190° C. |
| 28 | 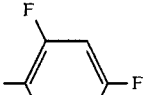 3-CF₃-C₆H₄ | CH₃ | 4-F-C₆H₄ | 173–174° C. |
| 29 |  3-CF₃-C₆H₄ | CH₃ |  2,4-F₂-C₆H₃ | 133–134° C. |
| 30 | 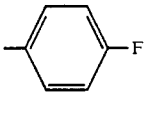 3-NO₂-C₆H₄ | CH₃ | C₆H₅ | 250–251° C. |
| 31 | 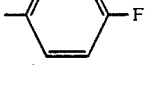 3-SCF₃-C₆H₄ | CH₃ | C₆H₅ | 116° C. |
| 32 | 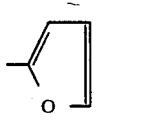 3-SCF₃-C₆H₄ | CH₃ | 4-F-C₆H₄ | 114° C. |
| 33 | 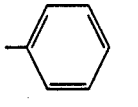 2-Cl-4-F-C₆H₃ | CH₃ | 4-F-C₆H₄ | 166–167° C. |
| 34 | 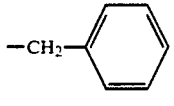 2-furyl | CH₃ | C₆H₅ | 96° C. |
| 35 | 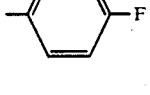 —CH₂—C₆H₅ | CH₃ | 4-F-C₆H₄ | 134° C. |
| 36 | 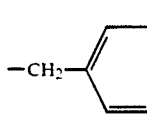 —CH₂—(3-CF₃-C₆H₄) | CH₃ | C₆H₅ | 77–78° C. |

TABLE 3-continued
| Ex. No. | R$^1$ | R$^2$ | Ar | melting point |
|---|---|---|---|---|
| 37 | 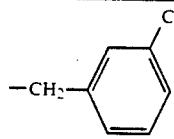 | CH$_3$ | 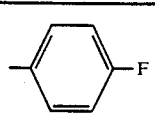 | 107° C. |
| 38 | 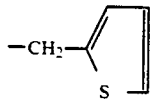 | CH$_3$ | 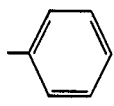 | 64–65° C. |
| 39 | 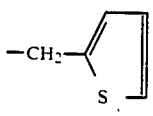 | CH$_3$ | 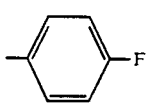 | 126–127° C. |
| 40 | 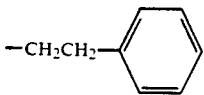 | CH$_3$ | 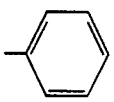 | 260° C. |
| 41 | 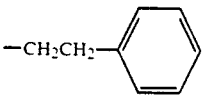 | CH$_3$ | 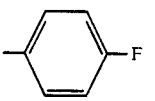 | 150° C. |
| 42 | 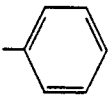 | —CH$_2$CF$_3$ | 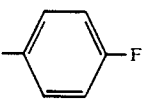 | 168° C. |
| 43 | —C$_3$H$_7$-n | CH$_3$ | 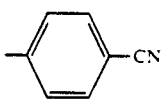 | 184–185° C. |
| 44 | —C$_3$H$_7$-n | CH$_3$ | 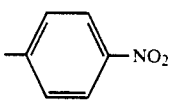 | 185–186° C. |
| 45 | —C$_3$H$_7$-n | CH$_3$ | 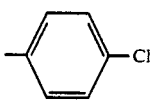 | 109–110° C. |
| 46 | —C$_3$H$_7$-n | CH$_3$ | 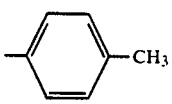 | 95–96° C. |
| 47 | —C$_3$H$_7$-n | CH$_3$ | 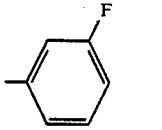 | 106–107° C. |
| 48 | —C$_4$H$_9$-n | CH$_3$ | 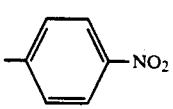 | 188–189° C. |
| 49 | —C$_4$H$_9$-n | CH$_3$ | 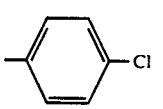 | 76–77° C. |

TABLE 3-continued

| Ex. No. | R¹ | R² | Ar | melting point |
|---|---|---|---|---|
| 50 | —C₄H₉-n | CH₃ | 4-CH₃-C₆H₄ | 84–85° C. |
| 51 | —CH₂-(3-CF₃-C₆H₄) | CH₃ | 4-Cl-C₆H₄ | 118–119° C. |
| 52 | —CH₂-(3-CF₃-C₆H₄) | CH₃ | 2-Cl-C₆H₄ | 78–79° C. |
| 53 | —CH₂-(3-CF₃-C₆H₄) | CH₃ | 3-Cl-C₆H₄ | 72–73° C. |

Preparation of the Starting Compounds

Example II-1

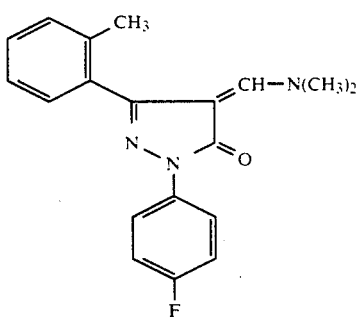

9.7 g (0.036 mol) of 1-(4-fluorophenyl)-3-(2-methylphenyl)-2-pyrazolin-5-one are dissolved in 40 ml of toluene and 5.7 g (0.047 mol) of N,N-dimethylformamide dimethyl acetal is added at room temperature. The reaction mixture is stirred at room temperature for 16 hours and is then strongly concentrated. The product is crystallized by addition of petroleum ether/ether.

9.8 g (84% of theory) of 4-(N,N-dimethylaminomethylidene-1-(4-fluorophenyl)-3-(2-methylphenyl)-pyrazolin-5-one of melting point 95° C. are obtained.

The starting compounds of the formula (II)

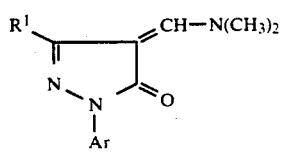

shown in Table 4 are obtained analogously to Example (II-1) and according to the general directions for preparation.

TABLE 4

| Ex. No. | R¹ | Ar | melting point |
|---|---|---|---|
| II-2 | —C₃H₇-n | 4-CF₃-C₆H₄ | 111–112° C. |
| II-3 | C₆H₅ | 2-F-C₆H₄ | 162° C. |
| II-4 | C₆H₅ | 3-F-C₆H₄ | 104° C. |
| II-5 | C₆H₅ | 4-Br-C₆H₄ | 187° C. |
| II-6 | C₆H₅ | 4-CH₃-C₆H₄ | 143° C. |
| II-7 | C₆H₅ | 4-OCH₃-C₆H₄ | 136° C. |
| II-8 | 2-F-C₆H₄ | 4-Br-C₆H₄ | 193° C. |

TABLE 4-continued

| Ex. No. | R¹ | Ar | melting point |
|---|---|---|---|
| II-9 | F (phenyl) | 4-CF₃-phenyl | 165° C. |
| II-10 | F (phenyl) | phenyl | 170° C. |
| II-11 | F (phenyl) | 4-CN-phenyl | 188° C. |
| II-12 | 4-F-phenyl | 4-F-phenyl | 103° C. |
| II-13 | Cl (phenyl) | phenyl | 112–113° C. |
| II-14 | Cl (phenyl) | 4-CF₃-phenyl | 142° C. |
| II-15 | Cl (phenyl) | 4-CN-phenyl | 201° C. |
| II-16 | Cl (phenyl) | 4-SO₂CF₃-phenyl | 150–151° C. |
| II-17 | 4-Cl-phenyl | phenyl | 170° C. |
| II-18 | Br (phenyl) | 4-F-phenyl | 92–94° C. |
| II-19 | Br (phenyl) | phenyl | 180° C. |
| II-20 | Br (phenyl) | 4-F-phenyl | 133° C. |
| II-21 | Br (phenyl) | 4-CF₃-phenyl | 144° C. |
| II-22 | CH₃ (phenyl) | phenyl | 139° C. |
| II-23 | CH₃ (phenyl) | 4-CN-phenyl | 143–144° C. |
| II-24 | CH₃ (phenyl) | 4-NO₂-phenyl | 126–128° C. |
| II-25 | CH₃ (phenyl) | 3,4-F₂-phenyl | 126–128° C. |
| II-26 | CH₃ (phenyl) | phenyl | 154° C. |
| II-27 | CH₃ (phenyl) | 4-F-phenyl | 143–144° C. |
| II-28 | CH₃ (phenyl) | 4-Br-phenyl | 142° C. |
| II-29 | CH₃ (phenyl) | 4-CH₃-phenyl | 130° C. |
| II-30 | CH₃ (phenyl) | 4-OCH₃-phenyl | 98–100° C. |

TABLE 4-continued

| Ex. No. | R¹ | Ar | melting point |
|---|---|---|---|
| II-31 | 2-OCH₃-phenyl | phenyl | 160° C. |
| II-32 | 3-OCH₃-phenyl | phenyl | 125° C. |
| II-33 | 2-CF₃-phenyl | phenyl | 106° C. |
| II-34 | 2-CF₃-phenyl | 4-F-phenyl | 55° C. |
| II-35 | 3-CF₃-phenyl | phenyl | 190° C. |
| II-36 | 3-CF₃-phenyl | 2-F-phenyl | 80° C. |
| II-37 | 3-CF₃-phenyl | 3-F-phenyl | 175° C. |
| II-38 | 3-CF₃-phenyl | 4-Br-phenyl | 172° C. |
| II-39 | 3-CF₃-phenyl | 4-CF₃-phenyl | 141° C. |
| II-40 | 3-CF₃-phenyl | 4-CH₃-phenyl | 145° C. |
| II-41 | 3-CF₃-phenyl | 4-OCH₃-phenyl | 141° C. |
| II-42 | 3-CN-phenyl | phenyl | 162–163° C. |
| II-43 | 3-CN-phenyl | 4-F-phenyl | 219° C. |
| II-44 | 3-SCF₃-phenyl | phenyl | 151° C. |
| II-45 | 3-SCF₃-phenyl | 4-F-phenyl | 153° C. |
| II-46 | 2-OCF₃-phenyl | phenyl | 87–88° C. |
| II-47 | 2-OCF₃-phenyl | 4-F-phenyl | 86–88° C. |
| II-48 | 2,3-Cl₂-phenyl | phenyl | 217° C. |
| II-49 | 2,3-Cl₂-phenyl | 4-F-phenyl | 167° C. |
| II-50 | 2,3-(CH₃)₂-phenyl | 4-F-phenyl | 187° C. |
| II-51 | 2,3-(OCH₃)₂-phenyl | 4-F-phenyl | 87° C. |
| II-52 | 2-Cl-4-F-phenyl | phenyl | 125° C. |

TABLE 4-continued

| Ex. No. | R¹ | Ar | melting point |
|---|---|---|---|
| II-53 | 2-Cl, 4-F-phenyl | 4-F-phenyl | 162° C. |
| II-54 | 2-furyl (5-methyl) | phenyl | 125° C. |
| II-55 | 2-thienyl (5-methyl) | phenyl | 136–138° C. |
| II-56 | 2-thienyl (5-methyl) | 4-F-phenyl | 145–147° C. |
| II-57 | 3-pyridyl | phenyl | 137–138° C. |
| II-58 | 3-pyridyl | 4-F-phenyl | 141° C. |
| II-59 | 1-naphthyl | phenyl | 133° C. |
| II-60 | 1-naphthyl | 4-F-phenyl | 146° C. |
| II-61 | —CH₂-(3-CF₃-phenyl) | phenyl | 125° C. |
| II-62 | —CH₂-(3-CF₃-phenyl) | 4-CF₃-phenyl | 144° C. |
| II-63 | —CH₂-(3-CF₃-phenyl) | 4-CH₃-phenyl | 115° C. |
| II-64 | —CH₂-(3-CF₃-phenyl) | 4-OCH₃-phenyl | 118° C. |
| II-65 | —CH₂-(3-CF₃-phenyl) | 3-Cl, 4-SO₂CF₃-phenyl | 114° C. |
| II-66 | —CH₂-(2-thienyl) | phenyl | 147° C. |
| II-67 | —CH₂-(2-thienyl) | 4-F-phenyl | 116–117° C. |
| II-68 | 2-OC₂H₅-phenyl | phenyl | 159–164° C. |
| II-69 | —CH₂CH₂-(2-phenyl)phenyl | phenyl | 99° C. |
| II-70 | 2-NO₂-phenyl | phenyl | 98° C. |
| II-71 | 3-(CH(CH₃)CN)-phenyl | phenyl | 165–166° C. |
| II-72 | 2-phenoxy, 3-F-phenyl | phenyl | 119° C. |

TABLE 4-continued

| Ex. No. | R¹ | Ar | melting point |
|---|---|---|---|
| II-73 | F | phenyl, 3-CHF₂ substituted | phenyl | 130° C. |
| II-74 | F | phenyl, 2,3-diF substituted | phenyl | 169–171° C. |
| II-75 | — | phenyl(2-F)-O-phenyl | 4-F-phenyl | 198° C. |
| II-76 | F | phenyl, 3-CHF₂ substituted | 4-F-phenyl | 139° C. |
| II-77 | — | phenyl-O-phenyl (3-) | 4-F-phenyl | 130° C. |
| II-78 | — | phenyl-O-phenyl (2-) | 4-F-phenyl | 133–136° C. |
| II-79 | — | 2-biphenyl | 4-F-phenyl | 40° C. |
| II-80 | 4-Cl-phenyl | 4-F-phenyl | 128° C. |
| II-81 | —CH₂—(3-CF₃-phenyl) | 4-Cl-phenyl | 144–145° C. |
| II-82 | —CH₂—(3-CF₃-phenyl) | 2-Cl-phenyl | 121–122° C. |
| II-83 | —CH₂—(3-CF₃-phenyl) | 3-Cl-phenyl | 105–106° C. |
| II-84 | —C₃H₇-n | 4-CN-phenyl | 162–163° C. |
| II-85 | —C₃H₇-n | 3-F-phenyl | 108–109° C. |
| II-86 | —C₄H₉-n | 4-CH₃-phenyl | — |
| II-87 | —C₄H₉-n | 4-NO₂-phenyl | 130–131° C. |

Use Examples

Example A

Pre-emergence Test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

A clearly superior activity and cultivated plant selectivity is shown in this test compared to the prior art by, for example, the compounds according to the following Preparation Examples: 1, 12, 13, 17, 18 and 37.

It is understood that the specification and examples are illustrative but not limitative of the present invention and that other embodiments within the spirit and scope of the invention will suggest themselves to those skilled in the art.

What is claimed is:

1. A pyrazolin-5-one of the formula

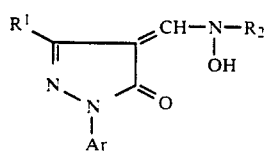

in which
R$^1$ represents phenyl or chlorophenyl,
R$^2$ represents alkyl, and
Ar represents phenyl or fluorophenyl.

2. A compound according to claim 1, wherein such compound is 1-(4-fluorophenyl)-3-phenyl-4-(N-methyl-N-hydroxyamino-methylidene)-pyrazolin-5-one of the formula

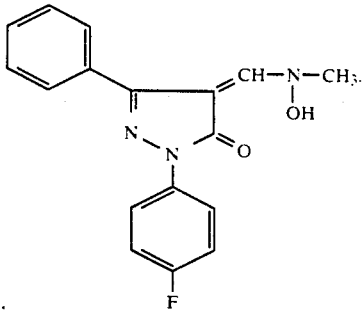

3. A compound according to claim 1, wherein such compound is 1-phenyl-3-(3-chlorophenyl)-4-N-methyl-N-hydroxyamino-methylidene)-pyrazolin-5-one of the formula

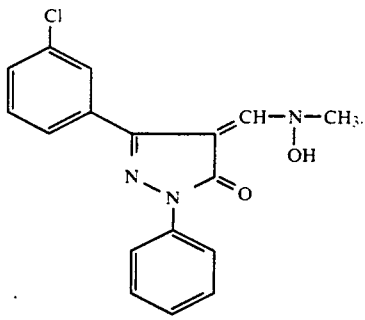

4. A compound according to claim 1, wherein such compound is 1-(4-fluorophenyl)-3-(3-chlorophenyl)-4-(N-methyl-N-hydroxyamino-methylidene)-pyrazolin-5-one of the formula

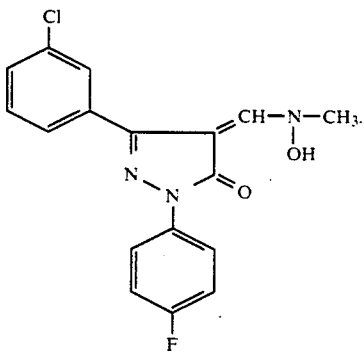

5. A herbicidal composition comprising a herbicidally effective amount of a compound according to claim 1 and a diluent.

6. A method of combating unwanted vegetation which comprises applying to such vegetation or to a locus from which it is desired to exclude such vegetation a herbicidally effective amount of a compound according to claim 1.

7. The method according to claim 13, wherein such compound is
1-(4-fluorophenyl)-3-phenyl-4-(N-methyl-N-hydroxyamino-methylidene)-pyrazolin-5-one,
1-phenyl-3-(3-chlorophenyl)-4-(N-methyl-N-hydroxyamino-methylidene)-pyrazolin-5-one or
1-(4-fluorophenyl)-3-(3-chlorophenyl)-4-(N-methyl-N-hydroxyamino-methylidene)-pyrazolin-5-one.

* * * * *

UNITED STATES PATENT AND TRADEMARK OFFICE
CERTIFICATE OF CORRECTION

PATENT NO. : 5,174,808

DATED : December 29, 1992

INVENTOR(S) : Wroblowsky et al.

It is certified that error appears in the above-identified patent and that said Letters Patent is hereby corrected as shown below:

Title Page        ABSTRACT: Lines 17-18 delete " alkylsusl-phinylalkyl " and substitute -- alkylsul-phinylalkyl --; line 26 delete " trifluoro-nethylphenyl " and substitute -- trifluoro-methylphenyl) --; next to last line delete " n- "

Col. 148, line 43      Delete " claim 13 " and substitute -- Claim 6 --

Signed and Sealed this

Thirty-first Day of May, 1994

Attest:

BRUCE LEHMAN

Attesting Officer      *Commissioner of Patents and Trademarks*